United States Patent
Pizarro et al.

(10) Patent No.: US 9,994,612 B2
(45) Date of Patent: *Jun. 12, 2018

(54) REFOLDING OF RECOMBINANT PROTEINS

(71) Applicant: Genentech, Inc., South San Francisco, CA (US)

(72) Inventors: Shelly Pizarro, San Carlos, CA (US); Ailen Sanchez, Foster City, CA (US); Charles H. Schmelzer, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/922,802

(22) Filed: Oct. 26, 2015

(65) Prior Publication Data

US 2016/0137690 A1 May 19, 2016

Related U.S. Application Data

(63) Continuation of application No. 13/668,182, filed on Nov. 2, 2012, now Pat. No. 9,200,030, which is a continuation of application No. 13/196,680, filed on Aug. 2, 2011, now abandoned, which is a continuation of application No. 11/777,997, filed on Jul. 13, 2007, now abandoned.

(60) Provisional application No. 60/830,831, filed on Jul. 14, 2006.

(51) Int. Cl.
| | |
|---|---|
| A23J 1/00 | (2006.01) |
| C07K 1/00 | (2006.01) |
| C07K 14/00 | (2006.01) |
| C07K 16/00 | (2006.01) |
| C07K 1/36 | (2006.01) |
| C07K 1/113 | (2006.01) |
| C07K 1/20 | (2006.01) |
| C07K 1/14 | (2006.01) |
| C07K 14/475 | (2006.01) |

(52) U.S. Cl.
CPC .............. *C07K 1/36* (2013.01); *C07K 1/1136* (2013.01); *C07K 1/14* (2013.01); *C07K 1/20* (2013.01); *C07K 14/00* (2013.01); *C07K 14/475* (2013.01)

(58) Field of Classification Search
None
See application file for complete search history.

(56) References Cited

U.S. PATENT DOCUMENTS

| | | | |
|---|---|---|---|
| 4,169,950 A | 10/1979 | Ferguson | |
| 4,710,473 A | 12/1987 | Morris | |
| 4,929,700 A | 5/1990 | Halenbeck et al. | |
| 5,077,392 A | 12/1991 | Rudolph et al. | |
| 5,332,671 A | 7/1994 | Ferrara et al. | |
| 5,700,665 A | 12/1997 | Legoux et al. | |
| 5,856,142 A | 1/1999 | Legoux et al. | |
| 6,632,425 B1 | 10/2003 | Li et al. | |
| 6,783,953 B1 | 8/2004 | Gordon et al. | |
| 7,611,711 B2 | 11/2009 | Alitalo et al. | |
| 2003/0229212 A1* | 12/2003 | Fahrner | C07K 1/18 530/417 |
| 2005/0119165 A1 | 6/2005 | Jue et al. | |

FOREIGN PATENT DOCUMENTS

| | | | |
|---|---|---|---|
| AR | 058625 A1 | 2/2008 | |
| EP | 0373325 A2 | 6/1990 | |
| EP | 0596459 A2 | 5/1994 | |
| EP | 0484401 B1 | 9/1996 | |
| EP | 1124941 B1 | 9/2003 | |
| EP | 1486511 A1 * | 12/2004 | ........... C07K 1/1133 |
| EP | 1973942 B1 | 2/2011 | |
| JP | S61195698 A | 8/1986 | |
| JP | 07039388 A | 2/1995 | |
| JP | H09501693 A | 2/1997 | |
| JP | H11130798 A | 5/1999 | |
| JP | 2004-505601 A | 2/2004 | |
| WO | WO-93/11240 A1 | 6/1993 | |
| WO | WO-95/07097 A1 | 3/1995 | |
| WO | WO-95/24473 A1 | 9/1995 | |
| WO | WO-96/02562 A1 | 2/1996 | |
| WO | WO-98/16551 A2 | 4/1998 | |
| WO | WO-99/42486 A1 | 8/1999 | |
| WO | WO-99/50302 A1 | 10/1999 | |
| WO | WO-01/55174 A2 | 8/2001 | |
| WO | WO-01/60861 A1 | 8/2001 | |
| WO | WO 0155174 A2 * | 8/2001 | ........... C07K 1/1133 |
| WO | WO-0155174 A2 * | 8/2001 | ........... C07K 1/1133 |
| WO | WO-01/87925 A2 | 11/2001 | |
| WO | WO-02/068455 A2 | 9/2002 | |
| WO | WO-2004/092393 A1 | 10/2004 | |
| WO | WO-2005/061712 A1 | 7/2005 | |

(Continued)

OTHER PUBLICATIONS

Tsumoto et al. Role of arginine in protein refolding, solubilization, and purification. Biotechnology Progress. Sep.-Oct. 2004; 20(5):1301-1308.*

Sherwood. Making bacterial extracts suitable for chromatography. Methods in Molecular Biology—Practical Protein Chromatography. 1992; 11:287-305.*

Menzella et al. High recovery of prochymosin from inclusion bodies using controlled air oxidation. Protein Expression and Purification, 2002; 25:248-255).*

Siemeister et al., "Expression of biologically active isoforms of the tumor angiogenesis factor VEGF in *Escherichia coli*," Biochem Biophys Res Commun. 222(2):249-55 (1996).

(Continued)

*Primary Examiner* — Vanessa L. Ford
*Assistant Examiner* — Sandra E Dillahunt
(74) *Attorney, Agent, or Firm* — Clark & Elbing LLP; Karen L. Elbing

(57) ABSTRACT

Processes are provided for recovering and purifying refolded recombinant proteins produced in heterologous host cells, which includes the step of refolding the protein in a high pH buffer.

6 Claims, 10 Drawing Sheets

(56) References Cited

FOREIGN PATENT DOCUMENTS

| WO | WO-2005/097827 A1 | 10/2005 |
| WO | WO-2006/001023 A2 | 1/2006 |
| WO | WO-2006/053568 A1 | 5/2006 |

OTHER PUBLICATIONS

Communication pursuant to Article 94(3) EPC for European Patent Application No. 07812919.4, dated Apr. 28, 2016 (5 pages).
Barzu et al., "Heparin-derived oligosaccharides: affinity for acidic fibroblast growth factor and effect on its growth-promoting activity for human endothelial cells," J Cell Physiol. 140(3):538-48 (1989).
Bolivar et al., "Construction and characterization of new cloning vehicles. II. A multipurpose cloning system," Gene. 2(2):95-113 (1977).
Brandner et al., "Investigating the effect of VEGF glycosylation on glycosaminoglycan binding and protein unfolding," Biochem Biophys Res Commun. 340(3):836-9 (2006).
Brinkmann et al., "Independent domain folding of Pseudomonas exotoxin and single-chain immunotoxins: influence of interdomain connections," Proc Natl Acad Sci U S A. 89(7):3075-9 (1992).
Buchner et al., "Renaturation, purification and characterization of recombinant Fab-fragments produced in *Escherichia coli*," Biotechnology (N Y). 9(2):157-62 (1991).
Burgess et al., "The heparin-binding (fibroblast) growth factor family of proteins," Annu Rev Biochem. 58:575-606 (1989).
Dabora et al., "Effect of polyanions on the refolding of human acidic fibroblast growth factor," J Biol Chem. 266(35):23637-40 (1991).
Ferrara et al., "Purification and cloning of vascular endothelial growth factor secreted by pituitary folliculostellate cells," Methods Enzymol. 198:391-405 (1991).
Ferrara, "Vascular endothelial growth factor: basic science and clinical progress," Endocr Rev. 25(4):581-611 (2004).
Gengrinovitch et al., "Glypican-1 is a VEGF165 binding proteoglycan that acts as an extracellular chaperone for VEGF165," J Biol Chem. 274(16):10816-22 (1999).
Heiring et al., "Folding screening assayed by proteolysis: application to various cystine deletion mutants of vascular endothelial growth factor," Protein Eng. 14(3):183-8 (2001).
Houck et al., "The vascular endothelial growth factor family: identification of a fourth molecular species and characterization of alternative splicing of RNA," Mol Endocrinol. 5(12):1806-14 (1991).
Ishihara et al., "Preparation of affinity-fractionated, heparin-derived oligosaccharides and their effects on selected biological activities mediated by basic fibroblast growth factor," J Biol Chem. 268(7):4675-83 (1993).
Kajio et al., "Stabilization of basic fibroblast growth factor with dextran sulfate," FEBS Lett. 306(2-3):243-6 (1992).
Keck et al., "Disulfide structure of the heparin binding domain in vascular endothelial growth factor: characterization of post-translational modifications in VEGF," Arch Biochem Biophys. 344(1):103-13 (1997).
Keyt et al., "Identification of vascular endothelial growth factor determinants for binding KDR and FLT-1 receptors. Generation of receptor-selective VEGF variants by site-directed mutagenesis," J Biol Chem. 271(10):5638-46 (1996).
Keyt et al., "The carboxyl-terminal domain (111-165) of vascular endothelial growth factor is critical for its mitogenic potency," J Biol Chem. 271(13):7788-95 (1996).
Kikuchi et al., "The nucleotide sequence of the promoter and the amino-terminal region of alkaline phosphatase structural gene (phoA) of *Escherichia coli*," Nucleic Acids Res. 9(21):5671-8 (1981).
Klagsbrun et al., "The fibroblast growth factor family: structural and biological properties," Prog Growth Factor Res. 1(4):207-35 (1989).
Lee et al., "Characterization of the gene encoding heat-stable toxin II and preliminary molecular epidemiological studies of enterotoxigenic *Escherichia coli* heat-stable toxin II producers," Infect Immun. 42(1):264-8 (1983).
Mach et al., "Partially structured self-associating states of acidic fibroblast growth factor," Biochemistry. 32(30):7703-11 (1993).
Menzella et al., "High recovery of prochymosin from inclusion bodies using controlled air oxidation," Protein Expr Purif. 25(2):248-55 (2002).
Picken et al, "Nucleotide sequence of the gene for heat-stable enterotoxin II of *Escherichia coli*," Infect Immun. 42(1):269-75 (1983).
Robinson et al., "The splice variants of vascular endothelial growth factor (VEGF) and their receptors," J Cell Sci. 114(Pt 5):853-65 (2001).
Scholtissek et al., "A cloning cartridge of lambda t(o) terminator," Nucleic Acids Res. 15(7):3185 (1987).
Scrofani et al., "Towards a Structure—Function Relationship for Vascular Endothelial Growth Factor-B (VEGF-B)," J Microbiol Biotechnol. 11(4):543-51 (2001).
Tsumoto et al., "Role of arginine in protein refolding, solubilization, and purification," Biotechnol Prog. 20(5):1301-8 (2004).
Yanofsky et al., "The complete nucleotide sequence of the tryptophan operon of *Escherichia coli*," Nucleic Acids Res. 9(24):6647-68 (1981).
English Translation of Decision of Rejection for Japanese Patent Application No. 2009-520923, dated Jul. 26, 2012 (3 pages).
English Translation of Notice of Preliminary Rejection for Korean Patent Application No. 10-2009-7002959, dated Dec. 20, 2013 (3 pages).
Examination Report for Canadian Patent Application No. 2,656,835, dated Nov. 5, 2013 (4 pages).
Rudolph et al., "In vitro folding of inclusion body proteins," FASEB J. 10(1):49-56 (1996).

\* cited by examiner

REFOLDING OF RECOMBINANT PROTEINS

CROSS-REFERENCE TO RELATED APPLICATIONS

This application is a continuation of U.S. application Ser. No. 13/668,182, filed Nov. 2, 2012, now U.S. Pat. No. 9,200,030, which is a continuation of U.S. application Ser. No. 13/196,680, filed an Aug. 2, 2011, now abandoned, which is a continuation of U.S. application Ser. No. 11/777,997, filed Jul. 13, 2007, now abandoned, which claims priority and the benefit of U.S. Provisional Application Ser. No. 60/830,831, filed Jul. 14, 2006, each of which is incorporated herein by reference.

FIELD OF THE INVENTION

This invention relates to methods for obtaining heterologous recombinant proteins produced in cell culture. The invention includes methods for recovering and purifying refolded recombinant proteins that have been produced in prokaryotic host cells and are present in these cells, typically in the periplasmic or intracellular space. The recombinant proteins produced in prokaryotic host cells can also be found as soluble proteins or as a mixture of soluble and insoluble proteins.

BACKGROUND

Many therapeutically relevant recombinant proteins are produced in a variety of host organisms. Most proteins can be expressed in their native form in eukaryotic hosts such as CHO cells. Animal cell culture generally requires prolonged growing times to achieve maximum cell density and ultimately achieves lower cell density than prokaryotic cell cultures (Cleland, J. (1993) *ACS Symposium Series 526, Protein Folding: In Vivo and In Vitro*, American Chemical Society). Additionally, animal cell cultures often require expensive media containing growth components that may interfere with the recovery of the desired protein. Bacterial host expression systems provide a cost-effective alternative to the manufacturing scale production of recombinant proteins. Numerous U.S. patents on general bacterial expression of recombinant proteins exist, including U.S. Pat. Nos. 4,565,785; 4,673,641; 4,795,706; and 4,710,473. A major advantage of the production method is the ability to easily isolate the product from the cellular components by centrifugation or microfiltration. See, e.g., Kipriyanov and Little, (1999) *Molecular Biotechnology*, 12: 173-201; and, Skerra and Pluckthun, (1988) *Science*, 240: 1038-1040.

However, bacterial expression systems such as *E. coli* lack the cellular machinery to facilitate proper refolding of the proteins and generally do not result in the secretion of large proteins into the culture media. Recombinant proteins expressed in bacterial host cells are often found as inclusion bodies consisting of dense masses of partially folded and misfolded reduced protein. See, e.g., Baneyx, (1999) *Current Opin. Biotechnology* 10:411-421; and, Villaverde and Carrio, (2003) *Biotech. Letts.* 25:1385-1395. Proteins may also be expressed without forming inclusion bodies. See, e.g., Id. Typically in inclusion bodies, the recombinant protein is generally inactive.

Additionally, refolding often produces misfolded and disulfide-linked dimers, trimers, and multimers. (Morris et al., (1990) *Biochem. J.*, 268:803-806; Toren et al., (1988) *Anal. Biochem.*, 169:287-299). This association phenomenon is very common during protein refolding, particularly at higher protein concentrations, and appears often to involve association through hydrophobic interaction of partially folded intermediates (Cleland and Wang, (1990) *Biochemistry*, 29:11072-11078).

Misfolding occurs either in the cell during fermentation or during the isolation procedure. Proteins recovered from periplasmic or intracellular space must be solubilized and the soluble protein refolded into the native state. See, e.g., Rudolph, *Renaturation of Recombinant, Disulfide-Bonded Proteins From "Inclusion Bodies"* in *Modern Methods in Protein- and Nucleic Acid Research* (Walter de Gruyter New York, 1990) pp. 149-172. In vitro methods for refolding the proteins into the correct, biologically active conformation are essential for obtaining functional proteins. Typical downstream processing of proteins recovered from inclusion bodies includes the dissolution of the inclusion body at high concentration of a denaturant such as urea followed by dilution of the denaturant to permit refolding to occur (see, U.S. Pat. Nos. 4,512,922; 4,511,502; and 4,511,503). See also, e.g., Rudolph and Lilie, (1996) *FASEB J.* 10:49-56; Fischer et al., (1993), *Biotechnology and Bioengineering*, 41:3-13; Misawa & Kumagai, (1999) *Biopolymers* 51:297-307; and, Clark, (1998) *Current Opinion in Biotechnology*, 9:157-163; and, Tsumoto et al., (2003) *Protein Expression and Purification* 28:1-8. Such recovery methods are regarded as being universally applicable, with minor modifications, to the recovery of biologically active recombinant proteins from inclusion bodies. These methods have been applied to heparin binding protein (HBP) such as VEGF (Siemeister et al. (1996) supra). These methods seek to eliminate random disulfide bonding prior to coaxing the recombinant protein into its biologically active conformation through its other stabilizing forces and may not eliminate improperly folded intermediates, provide homogenous populations of properly folded product, or provide sufficient amounts of the properly folded product.

Reversed micelles or ion exchange chromatography have been used to assist refolding of denatured proteins by enclosing a single protein within micelles or isolating them on a resin and then removing the denaturant (Hagen et al., (1990) *Biotechnol. Bioeng.* 35:966-975; Creighton (1985) in *Protein Structure Folding and Design* (Oxender, D. L. Ed.) pp. 249-251, New York: Alan R. Liss, Inc.). These methods have been useful in preventing protein aggregation and facilitating proper refolding. To alter the rate or extent of refolding, conformation-specific refolding has been performed with ligands and antibodies to the native structure of the protein (Cleland and Wang, (1993), in *Biotechnology*, (Rehm H.-J., and Reed G. Eds.) pp 528-555, New York, VCH). For example, creatine kinase was refolded in the presence of antibodies to the native structure (Morris et al., (1987) *Biochem. J.* 248:53-57). In addition to antibodies, ligands and cofactors have been used to enhance refolding. These molecules would be more likely to interact with the folding protein after formation of the native protein. Therefore, the folding equilibrium could be "driven" to the native state. For example, the rate of refolding of ferricytochrome c was enhanced by the extrinsic ligand for the axial position of the heme iron (Brems and Stellwagon, (1983) *J. Biol. Chem.* 258:3655-3661). Chaperone proteins and folding catalysts have also been used to assist with protein folding. See, e.g., Baneyx, (1999) *Current Opinion in Biotechnology*, 10:411-421; & Carrio & Villaverde, (2003) *FEBS Letters* 537:215-221. However, these methods are not always efficient or sufficient to produce quantities of protein product.

There is a need for new and more effective methods of folding and/or recovering recombinant proteins from a host cell culture, e.g., for the efficient and economical production of recombinant proteins in bacterial cell culture. These new and more effective methods provide for improved recovery of a highly purified biologically active properly refolded protein and that are generally applicable to manufacturing scale production of the proteins. The invention addresses these and other needs, as will be apparent upon review of the following disclosure.

SUMMARY OF THE INVENTION

The invention provides a method for recovering and purifying refolded recombinant proteins from cell culture. In particular the invention provides a method of recovering a recombinant protein from prokaryotic host cells, e.g., bacterial cells. The processes of the invention are broadly applicable to recombinant proteins. In certain embodiments, the recombinant protein is a growth factor, e.g., vascular endothelial growth factor (VEGF). In one embodiment, the growth factor is $VEGF_{165}$.

In one embodiment, a process includes: (a) isolating said recombinant protein from the prokaryotic cell culture; (b) solubilizing said protein in a first buffered solution, pH greater than 9, comprising a first chaotropic agent; (c) refolding said solubilized protein in a second buffered solution, pH>9 but ≤11, comprising a second chaotropic agent, two or more reducing agents and addition of air or oxygen for such a time and under such conditions that refolding of the recombinant protein occurs; and (d) recovering said refolded recombinant protein. In one embodiment, the first buffered solution and/or the second buffered solution further comprises arginine. In one embodiment, the first buffered solution comprises 1 M Urea, 300 mM arginine, 10 mM CHES, 5 mM EDTA, pH 11, final concentration. In another embodiment, the first buffered solution comprises 1 M Urea, 300 mM arginine, 10 mM TRIS, 5 mM EDTA, pH 11, final concentration. In one embodiment, the second buffered solution comprises two or more reducing agents, e.g., DTT and cysteine. In one embodiment, the second buffered solution comprises 1 M Urea, 15 mM cysteine, 2 mM DTT, 100 mM arginine, 10 mM CHES, 5 mM EDTA, pH 10, final concentration. In another embodiment, the second buffered solution comprises 1 M Urea, 15 mM cysteine, 0.5-2 mM DTT, 100 mM arginine, 10 mM TRIS, 5 mM EDTA, pH 10, final concentration.

In one embodiment, a process includes: (a) isolating said recombinant protein from the prokaryotic cell culture; (b) solubilizing and refolding said protein in a combo buffered solution, pH>9 but ≤11 with the addition of air or oxygen; and, (c) recovering said recombinant protein. In one embodiment, the combo buffered solution comprises 1 M Urea, 15 mM cysteine, 2 mM DTT, 100 mM arginine, 10 mM CHES, 5 mM EDTA, pH 10, final concentration. In another embodiment, the combo buffered solution comprises 1 M Urea, 15 mM cysteine, 0.5-2 mM DTT, 100 mM arginine, 10 mM TRIS, 5 mM EDTA, pH 10, final concentration.

The oxygen or air for the refold reaction can be provided by an air source or an oxygen enriched compressed gas supply. In one embodiment, a $k_{La}$ of 0.004 $min^{-1}$ is used, e.g., which represents a mixing rate of 200-400 rpm and sparging rate of 0.3 cc/min/L in a 2.5 L vessel containing a marine type impeller. In other embodiments, $k_{La}$=0.01 $min^{-1}$ or 0.1 $min^{-1}$ are used to produce refolded protein.

The solubilization and/or refolding can be done at a variety of temperatures. In one embodiment, the incubation temperature for the solubilization and/or refolding is room temperature. The incubation time can vary according to the recombinant protein being recovered and refolded. In one embodiment, the recombinant protein is incubated in the first buffered solution for at least 1 hour, or 1 to 2 hours. In one embodiment, the solubilized protein is incubated in the second buffered solution for about 3 to 24 hours. In one embodiment, the isolated recombinant protein is incubated in the combo buffered solution for 3 to 24 hours.

The invention additionally provides processes and methods for refolding of recombinant proteins either alone or in connection with the recovery of the recombinant protein as described herein. In a particular embodiment, purification methods include clarifying the solution containing the recombinant protein and contacting said refolded recombinant protein in the clarified solution with a mixed mode support, a cationic chromatographic support, a first hydrophobic interaction chromatographic support, and optionally, a second hydrophobic chromatographic support or an ion exchange support; and selectively recovering or eluting the refolded recombinant protein from each support. In one embodiment, clarifying the solution comprises adding detergent to a final concentration of 1%, adjusting pH to about 8.5-9.5, incubating solution for 1 to 10 hours at 25-30° C., centrifuging the solution; and filtering the liquid recovered from the centrifugation step. In one embodiment, the pH is about 8.7. In another embodiment, the pH is about 9.0. It is contemplated that the steps for recovery steps can be performed in any order, e.g., sequentially or altering the order of the chromatographic supports. In certain embodiments of the invention, methods are provided for recovering and purifying refolded recombinant proteins from manufacturing or industrial scale cell culture.

DETAILED DESCRIPTION

Definitions

Figure 1:
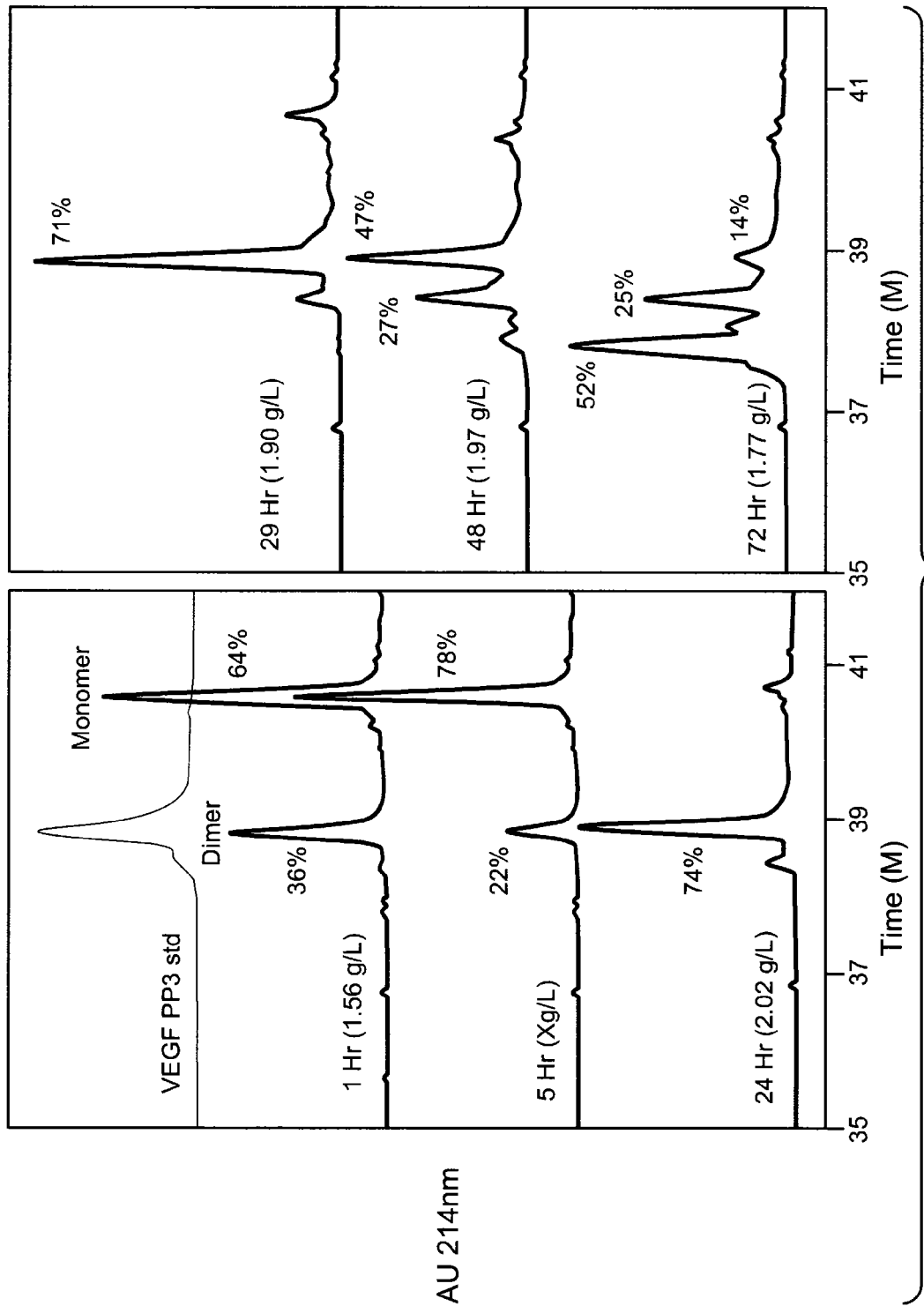
FIG. 1 illustrates an example a time course study of the refolding process as described herein, which was evaluated by rpHPLC chromatography.

As used herein, "polypeptide" refers generally to peptides and proteins from any cell source having more than about ten amino acids. "Heterologous" polypeptides are those polypeptides foreign to the host cell being utilized, such as a human protein produced by E. coli. While the heterologous polypeptide may be prokaryotic or eukaryotic, preferably it is eukaryotic, more preferably mammalian, and most preferably human. In certain embodiments of the invention, it is a recombinantly produced (e.g., a recombinant polypeptide or a recombinant protein).

Examples of mammalian polypeptides include molecules such as, e.g., a growth factor; a heparin-binding growth factor; vascular endothelial growth factor (VEGF), e.g., VEGF-A (isoforms), VEGF-B, VEGF-C and VEGF-D; a receptor and antibody to VEGF such as rhuFab V2 and bevacizumab, ranibizumab; an antibody to VEGF receptors; rennin; a growth hormone, including human growth hormone (hGH); bovine growth hormone; growth hormone releasing factor; parathyroid hormone; thyroid stimulating hormone; lipoproteins; 1-antitrypsin; insulin A-chain; insulin B-chain; proinsulin; thrombopoietin; follicle stimulating hormone; calcitonin; luteinizing hormone; glucagon; growth hormone receptors; growth hormone releasing protein (GHRF); LIV-1 (EP 1263780); TRAIL; clotting factors such as factor VIIIC, factor IX, tissue factor, and von Willebrands factor; Factor VIII; Factor VIII B domain; anti-tissue factor; anti-clotting factors such as Protein C; atrial naturietic factor; lung surfactant; a plasminogen activator, such as urokinase or human urine or tissue-type plasminogen activator (t-PA) and variants thereof; bombesin; thrombin; hemopoietic growth factor; tumor necrosis factor-alpha and -beta; antibodies to ErbB2 domain(s), enkephalinase; a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; inhibin; activin; receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF; cardiotrophins (cardiac hypertrophy factor) such as cardiotrophin-1 (CT-1); platelet-derived growth factor (PDGF) (A, B, C or D); fibroblast growth factor such as aFGF and bFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II) and their receptors such as IGFBP-1-IGFBP-6; des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; serum albumin, such as human serum albumin (HSA) or bovine serum albumin (BSA); colony stimulating factors (CSFs), e.g., M-CSF, GM-CSF, and G-CSF; interleukins (ILs), e.g., IL-1 to IL-10; anti-HER-2 antibody; Apo2 ligand; superoxide dismutase; anti-CD20; heregulin, anti-IgE, anti-CD11a, anti-CD18; tumor necrosis factor (TNF) and antibodies thereto, TNF receptor and related antibodies, TNF-receptor-IgG, TNF receptor associated factors (TRAF5) and inhibitors thereof, T-cell receptors; surface membrane proteins; decay accelerating factor; anti-TGF such as anti-TGF-beta; anti-activin; anti-inhibin; anti-Fas antibodies; Apo-2 ligand inhibitor; Apo-2 receptor; Apo-3; apoptotic factors; Ced-4; DcR3; death receptor and agonist antibodies (DR4, DR5); lymphotoxin (LT); prolactin; prolactin receptor; SOB proteins; WISP (wnt-induced secreted proteins); anti-NGF; DNase; hepatitis antigen; herpes simplex antigen; leptin; Toll protein, TIE ligands, CD40 and anti-CD40, immunoadhesins, subtilisin, hepatocyte growth factor (HGF), thrombopoietin (TPO); prostrate-specific cancer antigen (PSCA); viral antigen such as, for example, a portion of the AIDS envelope; transport proteins; homing receptors; addressins; regulatory proteins; antibodies; and fragments of any of the above-listed polypeptides. The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity. In certain embodiments of the invention, the recombinant polypeptide is a growth factor. In one embodiment, the recombinant polypeptide is the mammalian polypeptide VEGF. In another embodiment, the recombinant polypeptide is human VEGF (e.g., VEGF$_{165}$). In one embodiment, the recombinant polypeptide is not angiostatin. In one embodiment, the recombinant polypeptide is not IGF-1.

Figure 10:
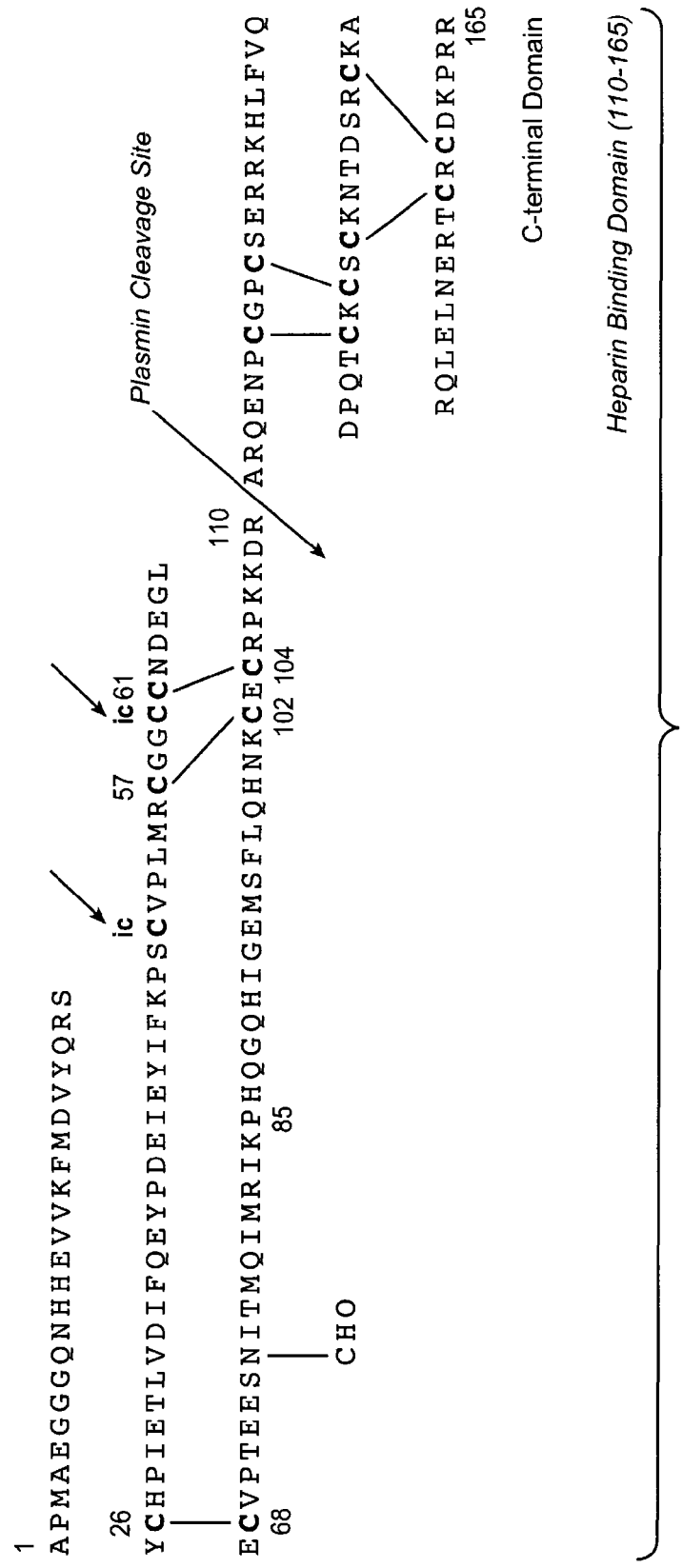
FIG. 10 illustrates the amino acid sequence of VEGF$_{165}$ with disulfide bonds indicated.

As used herein, "vascular endothelial growth factor", or "VEGF", refers to a mammalian growth factor derived originally from bovine pituitary follicular cells having the amino acid sequence disclosed in Castor, C. W., et al., (1991) *Methods in Enzymol.* 198:391-405, together with functional derivatives thereof having the qualitative biological activity of a corresponding native VEGF, including, but not limited to, the human VEGF amino acid sequence as reported in Houck et al., (1991) *Mol. Endocrin.* 5:1806-1814. See also, Leung et al. (1989) *Science,* 246:1306, and, Robinson & Stringer, (2001) *Journal of Cell Science,* 144 (5):853-865, U.S. Pat. No. 5,332,671. This is also referred to as VEGF-A. Other members of the family are indicated by a letter notation at the end of VEGF, e.g., VEGF-B, VEGF-C, or VEGF-D. The predominant form of VEGF or VEGF-A is a 165 amino acid homodimer having sixteen cysteine residues that form 7 intramolecular disulfide bonds and two intermolecular disulfide bonds. Alternative splicing has been implicated in the formation of multiple human VEGF polypeptides consisting of 121, 145, 165, 189 and 206 amino acids, however the VEGF$_{121}$ variant lacks the heparin binding domain of the other variants. All isoforms of VEGF share a common amino-terminal domain, but differ in the length of the carboxyl-terminal portion of the molecule. The preferred active form of VEGF, VEGF$_{165}$, has disulfide bonds between amino acid residues Cys26-Cys68; Cys57-Cys104; Cys61-Cys102; Cys117-Cys135; Cys120-Cys137; Cys139-Cys; 158; Cys146-Cys160 in each monomer. See FIG. 10. See also, e.g., Keck et al., (1997) *Archives of Biochemistry and Biophysics* 344(1):103-113. The VEGF$_{165}$ molecule is composed of two domains: an amino-terminal receptor-binding domain (amino acids 1-110 disulfide linked homodimer) and a carboxyl-terminal heparin-binding domain (residues 111-165). See, e.g., Keyt et al., (1996) *J. Biol. Chem.,* 271(13):7788-7795. In certain embodiments of the invention, the VEGF$_{165}$ isolated and purified is not glycosylated at residue 75 (Asn). See, e.g., Yang et al., (1998) *Journal of Pharm. & Experimental Therapeutics,* 284:103-110. In certain embodiments of the invention, the VEGF$_{165}$ isolated and purified is substantially undeamidated at residue Asn10. In certain embodiments of the invention, the $VEGF_{165}$ isolated and purified is a mixture of deamidated (at residue Asn10) and undeamidated protein, typically with majority of the protein being undeamidated. Since $VEGF_{165}$ is a homodimer, deamination can occur on one or both polypeptide chains.

The term "heparin binding protein" as used herein refers to a polypeptide capable of binding heparin (as herein defined). The definition includes the mature, pre, pre-pro, and pro forms of native and recombinantly produced heparin-binding proteins. Typical examples of heparin-binding proteins are "heparin binding growth factors," including but not limited to epidermal growth factor (EGF), platelet derived growth factor (PDGF), basic fibroblast growth factor (bFGF), acidic fibroblast growth factor (aFGF), vascular endothelial growth factor (VEGF), hepatocyte growth factor (HGF) (also known as scatter factor, SF), and nerve growth factor (NGF), IL-8, etc.

"Heparin" (also referred to as heparinic acid) is a heterogenous group of highly sulfated, straight-chain anionic mucopolysaccharides, called glycosaminoglycans. Although others may be present, the main sugars in heparin are: α-L-iduronic acid 2-sulfate, 2-deoxy-2-sulfamino-α-glucose 6-sulfate, β-D-glucuronic acid, 2-acetamido-2-deoxy-α-D-glucose, and L-iduronic acid. These and optionally other sugars are joined by glycosidic linkages, forming polymers of varying sizes. Due to the presence of its covalently linked sulfate and carboxylic acid groups, heparin is strongly acidic. The molecular weight of heparin varies from about 3,000 to about 20,000 daltons depending on the source and the method of determination. Native heparin is a constituent of various tissues, especially liver and lung, and mast cells in several mammalian species. Heparin and heparin salts (heparin sodium) are commercially available and are primarily used as anticoagulants in various clinical situations.

As used herein "properly folded" or "biologically active" VEGF or other recombinant protein and the like refers to a molecule with a biologically active conformation. The skilled artisan will recognize that misfolded and disulfide scrambled intermediates may have biological activity. In such a case the properly folded or biologically active VEGF or recombinant protein corresponds to the native folding pattern of the VEGF (described above) or other recombinant protein. For example, properly folded VEGF has the above noted disulfide pairs, in addition to two intermolecular disulfide bonds in the dimeric molecule, however other intermediates may be produced by bacterial cell culture. For properly folded VEGF, the two intermolecular disulfide bonds occur between the same residues, Cys51 and Cys60, of each monomer. See, e.g., WO98/16551. Biological activities of VEGF include, but are not limited to, e.g., promoting vascular permeability, promoting growth of vascular endothelial cells, binding to a VEGF receptor, binding and signaling through a VEGF receptor (see, e.g., Keyt et al., (1996) *Journal of Biological Chemistry,* 271(10):5638-5646), inducing angiogenesis, etc.

The terms "purified" or "pure recombinant protein" and the like refer to a material free from substances which normally accompany it as found in its recombinant production and especially in prokaryotic or bacterial cell culture. Thus the terms refer to a recombinant protein which is free of contaminating DNA, host cell proteins or other molecules associated with its in situ environment. The terms refer to a degree of purity that is at least about 75%, at least about 80%, at least about 85%, at least about 90%, at least about 95% or at least about 98% or more.

The terms "inclusion bodies" or "refractile bodies" refer to dense intracellular masses of aggregated polypeptide of interest, which constitute a significant portion of the total cell protein, including all cell components. In some cases, but not all cases, these aggregates of polypeptide may be recognized as bright spots visible within the enclosure of the cells under a phase-contrast microscope at magnifications down to 1,000 fold.

As used herein, the term "misfolded" protein refers to precipitated or aggregated polypeptides that are contained within refractile bodies. As used herein, "insoluble" or "misfolded" VEGF or other recombinant protein refers to precipitated or aggregated VEGF or recombinant protein that is contained within the periplasm or intracellular space of prokaryotic host cells, or is otherwise prokaryotic host cell associated, and assumes a biologically inactive conformation with mismatched or unformed disulfide bonds. The insoluble recombinant protein is generally, but need not be, contained in refractile bodies, i.e., it may or may not be visible under a phase contrast microscope.

As used herein, "chaotropic agent" refers to a compound that, in a suitable concentration in aqueous solution, is capable of changing the spatial configuration or conformation of polypeptides through alterations at the surface thereof so as to render the polypeptide soluble in the aqueous medium. The alterations may occur by changing, e.g., the state of hydration, the solvent environment, or the solvent-surface interaction. The concentration of chaotropic agent will directly affect its strength and effectiveness. A strongly denaturing chaotropic solution contains a chaotropic agent in large concentrations which, in solution, will effectively unfold a polypeptide present in the solution effectively eliminating the proteins secondary structure. The unfolding will be relatively extensive, but reversible. A moderately denaturing chaotropic solution contains a chaotropic agent which, in sufficient concentrations in solution, permits partial folding of a polypeptide from whatever contorted conformation the polypeptide has assumed through intermediates soluble in the solution, into the spatial conformation in which it finds itself when operating in its active form under endogenous or homologous physiological conditions. Examples of chaotropic agents include guanidine hydrochloride, urea, and hydroxides such as sodium or potassium hydroxide. Chaotropic agents include a combination of these reagents, such as a mixture of a hydroxide with urea or guanidine hydrochloride.

As used herein, "reducing agent" refers to a compound that, in a suitable concentration in aqueous solution, maintains free sulfhydryl groups so that the intra- or intermolecular disulfide bonds are chemically disrupted. Representative examples of suitable reducing agents include dithiothreitol (DTT), dithioerythritol (DTE), beta-mercaptoethanol (BME), cysteine, cysteamine, thioglycolate, glutathione, and sodium borohydride.

As used herein, "buffered solution" refers to a solution which resists changes in pH by the action of its acid-base conjugate components.

The "bacteria" for purposes herein include eubacteria and archaebacteria. In certain embodiments of the invention, eubacteria, including gram-positive and gram-negative bacteria, are used in the methods and processes described herein. In one embodiment of the invention, gram-negative bacteria are used, e.g., Enterobacteriaceae. Examples of bacteria belonging to Enterobacteriaceae include *Escherichia, Enterobacter, Erwinia, Klebsiella, Proteus, Salmonella, Serratia,* and *Shigella*. Other types of suitable bacteria include *Azotobacter, Pseudomonas, Rhizobia, Vitreoscilla,* and *Paracoccus*. In one embodiment of the invention, *E. coli* is used. Suitable *E. coli* hosts include *E. coli* W3110 (ATCC 27,325), *E. coli* 294 (ATCC 31,446), *E. coli* B, and *E. coli* X1776 (ATCC 31,537). These examples are illustrative rather than limiting, and W3110 is one example. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC177, or pKN410 are used to supply the replicon. See further below regarding examples of suitable bacterial host cells.

As used herein, the expressions "cell," "cell line," "strain," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A mixed mode column refers to a column with a resin that has both cation exchange properties as well as hydrophobic interactions.

Recombinant Proteins

Recombinant proteins, e.g., growth factors such as acidic fibroblast growth factor, basic fibroblast growth factor and vascular endothelial growth factor have been recovered and purified from a number of sources including bacteria (Salter D. H. et al., (1996) *Labor. Invest.* 74(2):546-556 (VEGF); Siemeister et al., (1996) *Biochem. Biophys. Res. Commun.* 222(2):249-55 (VEGF); Cao et al., (1996) *J. Biol. Chem.* 261(6):3154-62 (VEGF); Yang et al., (1994) *Gaojishu Tongxun,* 4:28-31 (VEGF); Anspach et al., (1995) *J. Chromatogr. A* 711(1):129-139 (aFGF and bFGF); Gaulandris (1994) *J Cell. Physiol.* 161(1):149-59 (bFGF); Estape and Rinas (1996) *Biotech. Tech.* 10(7):481-484 (bFGF); McDonald et al., (1995) *FASEB J.* 9(3):A410 (bFGF)). For example, the predominant active form of VEGF is a homodimer of two 165-amino acid polypeptides (VEGF-165). In this structure, each subunit contains 7 pairs of intrachain disulfide bonds and two additional pairs which effect the covalent linkage of the two subunits (Ferrara et al., (1991) *J. Cell. Biochem.* 47:211-218). The native conformation includes a strongly basic domain which has been shown to readily bind heparin (Ferrara et al (1991) supra). While covalent dimerization of VEGF is needed for effective receptor binding and biological activity (Potgens et al., (1994) *J. Biol. Chem.* 269:32879-32885; Claffey et al., (1995) *Biochim. et Biophys. Acta* 1246:1-9), the bacterial product potentially contains several misfolded and disulfide scrambled intermediates. Procedures are provided which are useful in isolating, purifying, and, reactivating proteins which appear in host cells in the form of "refractile bodies" and as soluble proteins as well.

Isolating Recombinant Protein

Insoluble, misfolded recombinant protein is isolated from prokaryotic host cells expressing the protein by any of a number of art standard techniques. For example, the insoluble recombinant protein is isolated in a suitable isolation buffer by exposing the cells to a buffer of suitable ionic strength to solubilize most host proteins, but in which the subject protein is substantially insoluble, or disrupting the cells so as to release the inclusion bodies or the protein form the periplasmic or intracellular space and make them available for recovery by, for example, centrifugation. This technique is well known and is described in, for example, U.S. Pat. No. 4,511,503. Kleid et al., disclose purification of refractile bodies by homogenization followed by centrifugation (Kleid et al., (1984) in *Developments in Industrial Microbiology*, (Society for Industrial Microbiology, Arlington, Va.) 25:217-235). See also, e.g., Fischer et al., (1993) *Biotechnology and Bioengineering* 41:3-13.

U.S. Pat. No. 5,410,026 describes a typical method for recovering protein from inclusion bodies and is summarized as follows. The prokaryotic cells are suspended in a suitable buffer. Typically the buffer consists of a buffering agent suitable for buffering at between pH 5 to 9, or about 6 to 8 and a salt. Any suitable salt, including NaCl, is useful to maintain a sufficient ionic strength in the buffered solution. Typically an ionic strength of about 0.01 to 2 M, or 0.1 to 0.2 M is employed. The cells, while suspended in this buffer, are disrupted or lysed using techniques commonly employed such as, for example, mechanical methods, e.g., Homogenizer (Manton-Gaulin press, Microfluidizer, or Niro-Soavi), a French press, a bead mill, or a sonic oscillator, or by chemical or enzymatic methods.

Examples of chemical or enzymatic methods of cell disruption include spheroplasting, which entails the use of lysozyme to lyse the bacterial wall (H. Neu et al., (1964) *Biochem. Biophys. Res. Comm.,* 17:215), and osmotic shock, which involves treatment of viable cells with a solution of high tonicity and with a cold-water wash of low tonicity to release the polypeptides (H. Neu et al., 1965 *J. Biol. Chem.,* 240(9):3685-3692). Sonication is generally used for disruption of bacteria contained in analytical scale volumes of fermentation broth. At larger scales high pressure homogenization is typically used.

After the cells are disrupted, the suspension is typically centrifuged at low speed, generally around 500 to 15,000×g, e.g., in one embodiment of the invention about 12,000×g is used, in a standard centrifuge for a time sufficient to pellet substantially all of the insoluble protein. Such times can be simply determined and depend on the volume being centrifuged as well as the centrifuge design. Typically about 10 minutes to 0.5 hours is sufficient to pellet the insoluble protein. In one embodiment the suspension is centrifuged at 12,000×g for 10 minutes.

The resulting pellet contains substantially all of the insoluble protein fraction. If the cell disruption process is not complete, the pellet may also contain intact cells or broken cell fragments. Completeness of cell disruption can be assayed by resuspending the pellet in a small amount of the same buffer solution and examining the suspension with a phase contrast microscope. The presence of broken cell fragments or whole cells indicates that further sonication or other means of disruption is necessary to remove the fragments or cells and the associated non-refractile polypeptides. After such further disruption, if required, the suspension is again centrifuged and the pellet recovered, resuspended, and reexamined. The process is repeated until visual examination reveals the absence of broken cell fragments in the pelleted material or until further treatment fails to reduce the size of the resulting pellet.

The above process can be employed whether the insoluble protein is intracellular or in the periplasmic space. In one embodiment of the invention, the conditions given herein for isolating recombinant protein are directed to inclusion bodies precipitated in the periplasmic space or intracellular space and relate particularly to VEGF. However, the processes and procedures are thought to be applicable to recombinant proteins in general with minor modifications as noted throughout the following text. In certain embodiments of the invention, the processes and procedures are applicable to manufacturing or industrial scale production, refolding, and purification of the recombinant protein.

In one embodiment, the isolated recombinant protein in the pellet is incubated in a first buffered solution sufficient to substantially solubilize the recombinant protein. This incubation takes place under conditions of concentration, incubation time, and incubation temperature that will allow solubilization of desired amount or substantially all the recombinant protein.

The first buffered solution comprises a buffering agent suitable for maintaining the pH range of the buffer at least about 9 or greater, with the typical range being 9-11. In one embodiment, the pH for VEGF is pH 11. Examples of suitable buffers that will provide a pH within this latter range include TRIS (Tris[hydroxymethyl]aminomethane), HEPPS (N-[2-Hydroxyethyl]piperazine-N'-[3-propane-sulfonic acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In one embodiment, the buffer herein includes CHES and arginine at about pH 11. In another embodiment, the buffer herein includes Tris and arginine at about pH 11. In one embodiment, the buffer herein includes CHES at about pH 11. In another embodiment, the buffer herein includes Tris at about pH 11. In certain embodiments, the first buffered solution includes a chaotropic agent.

Chaotropic agents suitable for practicing this invention include, e.g., urea and salts of guanidine or thiocyanate, e.g., urea, guanidine hydrochloride, sodium thiocyanate, etc. The amount of chaotropic agent necessary to be present in the buffer is an amount sufficient to unfold the recombinant protein in solution. In certain embodiments of the invention, a chaotrope is present at about between about 0.5-5 molar. In one embodiment of the invention, the chaotropic agent is urea at about 1 M.

The concentration of the protein in the buffered solution must be such that the protein will be substantially solubilized as determined by optical density. The exact amount to employ will depend on, e.g., the concentrations and types of other ingredients in the buffered solution, particularly the protein concentration, chaotropic agent, and the pH of the buffer. In one embodiment of the invention, the concentration of recombinant protein is in the range of 0.5-5.5 mg per ml, or 1.5-5.0 mg/ml. The solubilization is typically carried out at about 0-45° C., or about 2-40° C., or about 20-40° C., or about 23-37° C., or about 25-37° C., or about 25° C. for at least about one to 24 hours. Typically, the temperature is not apparently affected by salt, reducing agent and chaotropic agent levels. In certain embodiments, the solubilization is carried out at atmospheric pressure.

Measurement of the degree of solubilization in the buffered solution can be determined and is suitably carried out, for example, by turbidity determination, by analyzing fractionation between the supernatant and pellet after centrifugation, on reduced SDS-PAGE gels, by protein assay (e.g., the Bio-Rad protein assay kit), or by HPLC.

Optionally, the disrupted cells are not centrifuged but are diluted, e.g., 1:4, 1:6, 1:8 in a second buffered solution described herein (refolding buffer). This incubation takes place under conditions of concentration, incubation time, and incubation temperature that will allow solubilization and refolding of the recombinant protein. In one embodiment, about 30% or more of recombinant protein is solubilized and refolded.

Refolding Recombinant Proteins

After the polypeptide is solubilized or, alternatively, the cells are disrupted, it is placed or diluted into a second buffered solution containing at least one reducing agent, and a chaotropic agent, at concentration which allow for refolding of the recombinant protein, along with the addition of air or oxygen, e.g., using a constant volumetric mass transfer coefficient $k_{La}$=0.004 to 0.1 min$^{-1}$ (e.g., for a 2.5 L vessel with a marine type impeller, air sparging rate is 0.3-10 cc/min/L, 0.3-3 cc/min/L, or 1 cc/min/L, or 25 cc/min/L with mixing speed of 200-400 rpm). The oxygen or air for the refold reaction can be provided by an air source or an oxygen enriched compressed gas supply. The efficiency of mass transfer from the gas phase to the liquid phase is controlled by agitation, sparging and pressurization and is captured by the volumetric mass transfer coefficient, $k_{La}$. See, e.g., Blanch, & Clark, Biochemical engineering, Marcel Dekker, New York, 1997; and, Aunins, & Henzler, *Aeration in cell culture bioreactors*, in *Biotechnology: A multi-volume comprehensive treatise*, G. Stephanopoulos, Ed., Weinheim, New York, 1993, pp. 219-281. In one embodiment, a $k_{La}$ of 0.004 min$^{-1}$ is used representing a mixing rate of 200-400 rpm and sparging rate of 0.3 cc/min/L in a 2.5 L vessel containing a marine type impeller. In other embodiments, $k_{La}$=0.01 min$^{-1}$ or 0.1 min$^{-1}$ are used to produce properly folded protein.

In certain embodiments of the invention, the second buffered solution contains two or more reducing agents. The polypeptide may be diluted with the refolding buffer, e.g., at least five fold, or at least about ten fold, or about 20 fold, or about 40 fold. The conditions of this second incubation of the soluble, unfolded protein will generally be such that desired amount or substantial or complete refolding of the protein will take place. The exact conditions will depend on, for example, the pH of the buffer and the types and concentrations of chaotropic and reducing agents present. The incubation temperature is generally about 0-40° C. and the incubation will generally be carried out for at least about 1 hour to about 48 hours to effect refolding. In certain embodiments, the reaction is carried out, e.g., at about 0-45° C., or about 2-40° C., or about 20-40° C., or about 23-37° C., or about 25-37° C., or about 25° C., for at least about 3 hours, for at least about 10 hours, or between about 3 and 30 hours, or between about 3 and 24 hours. In certain embodiments, the reaction is carried out at atmospheric pressure.

The second buffered solution comprises a buffering agent suitable for maintaining the pH range of the buffer at least about 9 or greater than 9, with the typical range being 9-11, a chaotropic agent, and at least one reducing agent. In certain embodiments, the second buffered solution comprises two or more reducing agents. In one embodiment, the pH for VEGF is pH 10. Examples of suitable buffers that will provide a pH within this latter range include TRIS. (Tris[hydroxymethyl] aminomethane), HEPPS (N-[2-Hydroxyethyl]piperazine-N'-[3-propane-sulfonic acid]), CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), arginine, lysine, and sodium borate. In one embodiment, the second buffered solution herein comprises CHES and arginine at about pH 10 (at about a concentration of 10 mM and 100 mM final concentration, respectively), with two or more reducing agents and at least one chaotropic agent. In another embodiment, the second buffered solution herein comprises Tris and arginine at about pH 10 (at about a concentration of 10 mM and 100 mM final concentration, respectively), with two or more reducing agents and at least one chaotropic agent.

Arginine (or another positively charged amino acid), e.g., L-arginine/HCl, can be present in the first buffered solution and the second buffered solution. In certain embodiments of the invention, the concentration of arginine is e.g., about 50-500 mM, about 75-300 mM, or about 100-300 mM, or about 100 mM or 300 mM final concentration, etc. In certain embodiments of the invention, the protein is in a first buffered solution at pH greater than 9 and 0.5-3 M urea, 50-500 mM arginine and 5 mM EDTA, final concentration. In one embodiment, 10 mM CHES final concentration is used. In another embodiment, 10 mM Tris final concentration is used. In one embodiment, the first buffered solution comprises 1 M Urea, 300 mM arginine, 10 mM CHES, 5 mM EDTA, pH 11, final concentration. In another embodiment, the first buffered solution comprises 1 M Urea, 300 mM arginine, 10 mM Tris, 5 mM EDTA, pH 11, final concentration. In certain embodiments of the invention, the protein is in a second buffered solution (refolding buffered solution) at pH>9 but ≤11 containing 0.5-3 M urea, 50-500 mM arginine, 0.25-1 mM DTT, 5-20 mM cysteine, and 2-10 mM EDTA, final concentration. In one embodiment, 10 mM CHES final concentration is used. In another embodiment, 10 mM Tris final concentration is used. In one embodiment, the protein is in a refolding buffer solution with 1 M urea, 15 mM cysteine, 2 mM DTT, 100 mM arginine, 10 mM CHES, 5 mM EDTA, pH 9-10, final concentration. In another embodiment, the protein is in a refolding buffer solution with 1 M urea, 15 mM cysteine, 0.5-2 mM DTT, 100 mM arginine, 10 mM Tris, 5 mM EDTA, pH 9-10, final concentration.

As noted, the solution also contains at least one reducing agent. Examples of suitable reducing agents include, but are not limited to, dithiothreitol (DTT), β-mercaptoethonol (BME), cysteine, DTE, etc. The amount of reducing agent to be present in the buffer will depend mainly on the type of reducing agent and chaotropic agent, the type and pH of the buffer employed, the amount of oxygen entrained in or introduced to the solution, and the concentration of the protein in the buffer. For example, the reducing agent is suitably selected from those described above in the concentration range of about 0.5 to about 20 mM for cysteine, 0.25-3.0 mM for DTT (e.g., 0.5-2 mM DTT), and less than about 0.2 mM for BME. In one embodiment of the invention, there are two or more reducing agents, e.g., DTT at about 0.5-2 mM and 0.5 to about 20 mM cysteine. Whereas DTT and BME can be used in connection with the procedures provided herein for recombinant proteins in general, a combination of cysteine at about 15 mM and DTT as described above is an example for the recovery of VEGF. In one embodiment, the reducing agent is DTT at about 2 mM, with 15 mM cysteine, final concentration. In another embodiment, the reducing agent is DTT at about 0.5 mM, with 15 mM cysteine, final concentration.

The second buffered solution contains at least one chaotropic agent at a concentration such that refolding of the recombinant protein occurs. Generally a chaotrope is present at about between about 0.5 and 2 molar final concentration. In one embodiment of the invention, the chaotropic agent herein is urea at about 0.5-2 M, 0.5-2 M, or about 1 M, final concentration. In another embodiment of the invention, the chaotropic agent is guanidine hydrochloride at about 0.1-1 M final concentration.

The refolding buffer can optionally contain additional agents such as any of a variety of non-ionic detergents such as TRITON™ X-100, NONIDET™ P-40, the TWEEN™ series and the BRIJ™ series. The non-ionic detergent is present at about between 0.01% and 1.0% final concentration. In one example, the concentrations for non ionic detergent are between about 0.025% and 0.05%, or about 0.05% final concentration.

The degree of refolding is suitably determined by high performance liquid chromatography (HPLC) analysis using e.g., rpHPLC chromatography column, a cation exchange HPLC (SP-5PW TSK gel column, Tosoh Bioscience LLC), or other appropriate heparin affinity column. Increasing correctly folded recombinant peak size in the cation exchange HPLC assay or Heparin binding HPLC assay directly correlates with increasing amounts of folded, biologically active recombinant protein present in the buffer. The incubation is carried out to maximize the ratio of correctly folded recombinant protein to misfolded recombinant protein recovered, as determined by rpHPLC assay.

In one embodiment, the quality and quantity of properly-folded VEGF is assessed using a heparin-binding assay. Samples containing the diluted recombinant protein are loaded on a e.g., Heparin-5PW column (7.5×75 mm, Tosoh Biosciences LLC, Tokyo, Japan) or other suitable heparin affinity column. For example, the Heparin-5PW column is equilibrated in 10 mM sodium phosphate, pH 7.4 containing 0.15 M sodium chloride. At a flow rate of 1 ml/min or 2 ml/min, the column is eluted using a linear gradient from 0.15-2 M sodium chloride in, 10 mM sodium phosphate, pH 7.4 over 10 minutes. The eluant is monitored at 280 nm. In one embodiment, the protein is recovered in a single peak corresponding to the biologically active properly refolded VEGF. In one embodiment of the invention, an assay for determining properly refolded VEGF is RPHPLC. Disulfide linkages can optionally be confirmed by peptide map. Circular dichroism can also be used in for determining 2 & 3D structure/folding.

In one embodiment, solubilization and refolding is performed in one step. After obtaining the disrupted cell pellet, it is placed or diluted into the second buffered solution described above (in this case entitled a combo buffered solution). The polypeptide may be diluted with the combo buffered solution, e.g., at least five fold, or at least about ten fold, or about 20 fold, or about 40 fold. The conditions of this incubation of the pellet will generally be such that desired amount or substantial or complete solubilization and refolding of the protein will take place, with the addition of air or oxygen. In one embodiment, a $k_1$ of 0.004 min$^{-1}$ is used representing a mixing rate of 200-400 rpm and sparging rate of 0.3 cc/min/L in a 2.5 L vessel containing a marine type impeller. In other embodiments, $k_1$=0.01 min$^{-1}$ or 0.1 min$^{-1}$ are used to produce properly folded protein. The exact conditions will depend on, for example, the pH of the buffer and the types and concentrations of chaotropic and reducing agents present. The incubation temperature is generally about 0-40° C. and the incubation will generally be carried out for at least about 1 to 48 hours to effect solubilization and refolding. The reaction is carried out, e.g., at about 0-45° C., or about 2-40° C., or about 20-40° C., or about 23-37° C., or about 25-37° C., or about 25° C., for at least about 3 hours, for at least about 10 hours, or between about 3 and 48 hours, or between about 3 and 30 hours. In certain embodiments, the reaction is carried out at atmospheric temperature.

Recovery and Purification of Recombinant Proteins

Although recovery and purification of the recombinant protein can employ various methods and known procedures for the separation of such proteins such as, for example, salt and solvent fractionation, adsorption with colloidal materials, gel filtration, ion exchange chromatography, affinity chromatography, immunoaffinity chromatography, electrophoresis and high performance liquid chromatography (HPLC), an example of a clarification step and a multi-step chromatographic procedure is described. The clarification step comprises adding detergent to a final concentration of 1% (e.g., TRITON™ X-100), adjusting pH to about 8.5-9.5 (or about 8.7 or about 9), incubating solution for 1 to 10 hours at 25-30° C., centrifuging the solution; and filtering liquid recovered from the centrifugation step. The multi-step chromatographic procedure comprises contacting said refolded recombinant protein with a mixed mode resin, a cationic chromatographic support, a first hydrophobic chromatography support, and optionally, a second hydrophobic chromatography support or an ion exchange support; and selectively recovering or eluting the recombinant protein from each support. It is contemplated that the steps of either procedure can be performed in any order. In one embodiment of the invention, the steps are performed sequentially.

A suitable first step in the further recovery and purification of the recombinant protein characteristically provides for the concentration of the recombinant protein and a reduction in sample volume. For example, the second incubation step described above, may result in a large increase in the volume of the recovered recombinant protein and concomitant dilution of the protein in the refolding buffer. Suitable first chromatographic supports provide a reduction in volume of recovered recombinant protein and may advantageously provide some purification of the protein from unwanted contaminating proteins. Suitable first chromatographic steps include chromatographic supports which can be eluted and loaded directly onto a second chromatographic support.

Exemplary first chromatographic supports include, but are not limited to, mixed mode resin (e.g., CAPTOMMC™, GE Healthcare, or MEP HYPERCEL™, Pall Corporation), hydroxyapatite chromatographic supports, e.g., CHT™ ceramic type I and type II (formally known as MACRO-PREP® ceramic), BIO-GEL® HT, BIO-GEL® HTP, Biorad, Hercules, Calif., etc.; metal chelating chromatographic supports consisting of an inert resin of immobilized metal ions such as copper, nickel, etc.; as well as non-derivatized silica gels. In one embodiment of the invention, the first chromatographic supports for the purification and recovery of VEGF are mixed ion exchange chromatographic supports. Elution from the first chromatographic support is accomplished according to art standard practices. Suitable elution conditions and buffers will facilitate the loading of the eluted recombinant protein directly onto the cationic chromatographic support as described below.

Various anionic constituents may be attached to matrices in order to form cationic supports for chromatography. Anionic constituents include carboxymethyl, sulfethyl groups, sulfopropyl groups, phosphate and sulfonate (S). Cellulosic ion exchange resins such as SE52 SE53, SE92, CM32, CM52, CM92, P11, DE23, DE32, DE52, EXPRESS ION™ S and EXPRESS ION™ C are available from Whatman LTD, Maidstone Kent U.K. SEPHAROSE™ and SEPHAROSE™ based and cross linked ion exchangers are also known under the product names CM SEPHADEX™ C-25, CM SEPHADEX™ C-50 and SP SEPHADEX™ C-25 SP SEPHADEX™ C-50 and SP-SEPHAROSE™ High Performance, SP-SEPHAROSE™-XL SP-SEPHAROSE™ Fast Flow, CM-SEPHAROSE™ Fast Flow, and CM-SEPHAROSE™, CL-6B, all available from Pharmacia AB. Examples of ion exchangers for the practice of the invention include but are not limited to, e.g., ion exchangers under the product names MACROPREP™ such as for example MACROPREP™ S support, MACROPREP™ High S support and MACROPREP™ CM support from BioRad, Hercules, Calif.

Elution from cationic chromatographic supports is generally accomplished by increasing salt concentrations. Because the elution from ionic columns involves addition of salt and because, as mentioned herein, HIC is enhanced in salt concentration the introduction of HIC step following the ionic step or other salt step is optionally used. In one embodiment of the invention, a cationic exchange chromatographic step precedes at least the HIC step, e.g., a first hydrophobic interaction chromatographic support and/or a second hydrophobic interaction.

Hydrophobic columns can be used in the purification of the recombinant protein, e.g., in the $2^{nd}$, $3^{rd}$, and/or $4^{th}$ purification steps. Hydrophobic interaction chromatography is well known in the art and is predicated on the interaction of hydrophobic portions of the molecule interacting with hydrophobic ligands attached to "chromatographic supports." A hydrophobic ligand coupled to a matrix is variously referred to as an HIC chromatographic support, HIC gel, or HIC column and the like. It is further appreciated that the strength of the interaction between the protein and the HIC column is not only a function of the proportion of non-polar to polar surfaces on the protein but of the distribution of the non-polar surfaces as well.

A number of matrices may be employed in the preparation of HIC columns. The most extensively used is agarose, although silica and organic polymer resins may be used. Useful hydrophobic ligands include but are not limited to alkyl groups having from about 2 to about 10 carbon atoms, such as butyl, propyl, or octyl, or aryl groups such as phenyl. Conventional HIC supports for gels and columns may be obtained commercially from suppliers such as Pharmacia, Uppsala, Sweden under the product names butyl-SEPHAROSE™, buty-SEPHAROSE™-Fast Flow, phenyl-SEPHAROSE™ CL-4B, octyl SEPHAROSE™ FF and phenyl SEPHAROSE™ FF and Tosoh Corporation, Tokyo, Japan under the product names TOYOPEARL™ butyl 650M (Fractogel TSK Butyl-650) or TSK-GEL phenyl 5PW.

Ligand density is an important parameter in that it influences not only the strength of the interaction of the protein but the capacity of the column as well. The ligand density of the commercially available phenyl or octyl phenyl gels is on the order of 5-40 μmoles/ml gel bed. Gel capacity is a function of the particular protein in question as well as pH, temperature and salt concentration but generally can be expected to fall in the range of 3-20 mg/ml gel.

The choice of particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be different owing to the possibility of pi-pi interaction with aromatic groups of the protein.

Adsorption of the protein to a HIC column is favored by high salt concentration, but the actual concentration can vary over a wide range depending of the nature of the protein and the particular HIC ligand chosen. In general salt concentration between about 1 and 4 M are useful.

Elution from an HIC support, whether stepwise or in the form of a gradient, can be accomplished in a variety of ways such as a) by changing the salt concentration, b) by changing the polarity of the solvent or c) by adding detergents. By decreasing salt concentrations adsorbed proteins are eluted in order of increasing hydrophobicity. Changes in polarity may be effected by additions of solvents such as ethylene glycol or isopropanol thereby decreasing the strength of the hydrophobic interactions. Detergents function as displacers of proteins and have been used primarily in connection with the purification of membrane proteins.

Examples of methods for purifying VEGF is described herein below, e.g., see Examples IV and V.

Expressing Recombinant Protein

In brief, expression vectors capable of autonomous replication and protein expression relative to the host prokaryotic cell genome are introduced into the host cell. Construction of appropriate expression vectors is well known in the art including the nucleotide sequences of the recombinant proteins described herein. See, e.g., Sambrook et al., *Molecular Cloning, A Laboratory Manual*, Cold Spring Harbor Laboratory Press (Cold Spring Harbor, N.Y.) (2001); Ausubel et al., *Short Protocols in Molecular Biology*, Current Protocols John Wiley and Sons (New Jersey) (2002); and, Baneyx, (1999) *Current Opinion in Biotechnology*, 10:411-421. Appropriate prokaryotic cell, including bacteria, expression vectors are available commercially through, for example, the American Type Culture Collection (ATCC), Rockville, Md. Methods for the large scale growth of prokaryotic cells, and especially bacterial cell culture are well known in the art and these methods can be used in the context of the invention.

For example, prokaryotic host cells are transfected with expression or cloning vectors encoding the recombinant protein of interest and cultured in conventional nutrient media modified as appropriate for inducing promoters, selecting transformants, or amplifying the genes encoding the desired sequences. The nucleic acid encoding the polypeptide of interest is suitably RNA, cDNA, or genomic DNA from any source, provided it encodes the polypeptide(s) of interest. Methods are well known for selecting the appropriate nucleic acid for expression of heterologous polypeptides (including variants thereof) in microbial hosts. Nucleic acid molecules encoding the polypeptide are prepared by a variety of methods known in the art. For example, a DNA encoding VEGF is isolated and sequenced, e.g., by using oligonucleotide probes that are capable of binding specifically to the gene encoding VEGF.

The heterologous nucleic acid (e.g., cDNA or genomic DNA) is suitably inserted into a replicable vector for expression in the microorganism under the control of a suitable promoter. Many vectors are available for this purpose, and selection of the appropriate vector will depend mainly on the size of the nucleic acid to be inserted into the vector and the particular host cell to be transformed with the vector. Each vector contains various components depending on the particular host cell with which it is compatible. Depending on the particular type of host, the vector components generally include, but are not limited to, one or more of the following: a signal sequence, an origin of replication, one or more marker genes, a promoter, and a transcription termination sequence.

In general, plasmid vectors containing replicon and control sequences that are derived from species compatible with the host cell are used in connection with microbial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., (1977) *Gene*, 2: 95). pBR322 contains genes for ampicillin and tetracycline resistance and thus provides easy means for identifying transformed cells. The pBR322 plasmid, or other bacterial plasmid or phage, also generally contains, or is modified to contain, promoters that can be used by the host for expression of the selectable marker genes.

(i) Signal Sequence

Polypeptides of the invention may be produced recombinantly not only directly, but also as a fusion polypeptide with a heterologous polypeptide, which is typically a signal sequence or other polypeptide having a specific cleavage site at the N-terminus of the mature protein or polypeptide. The heterologous signal sequence selected typically is one that is recognized and processed (i.e., cleaved by a signal peptidase) by the host cell. For prokaryotic host cells that do not recognize and process the native polypeptide signal sequence, the signal sequence is substituted by a prokaryotic signal sequence selected, for example, from the group of the alkaline phosphatase, penicillinase, lpp, or heat-stable enterotoxin II leaders.

(ii) Origin of Replication Component

Expression vectors contain a nucleic acid sequence that enables the vector to replicate in one or more selected host cells. Such sequences are well known for a variety of microbes. The origin of replication from the plasmid pBR322 is suitable for most Gram-negative bacteria such as *E. coli*.

(iii) Selection Gene Component

Expression vectors generally contain a selection gene, also termed a selectable marker. This gene encodes a protein necessary for the survival or growth of transformed host cells grown in a selective culture medium. Host cells not transformed with the vector containing the selection gene will not survive in the culture medium. This selectable marker is separate from the genetic markers as utilized and defined by this invention. Typical selection genes encode proteins that (a) confer resistance to antibiotics or other toxins, e.g., ampicillin, neomycin, methotrexate, or tetracycline, (b) complement auxotrophic deficiencies other than those caused by the presence of the genetic marker(s), or (c) supply critical nutrients not available from complex media, e.g., the gene encoding D-alanine racemase for Bacilli.

One example of a selection scheme utilizes a drug to arrest growth of a host cell. In this case, those cells that are successfully transformed with the nucleic acid of interest produce a polypeptide conferring drug resistance and thus survive the selection regimen. Examples of such dominant selection use the drugs neomycin (Southern et al., (1982) *J. Molec. Appl. Genet.*, 1: 327), mycophenolic acid (Mulligan et al., (1980) *Science* 209: 1422) or hygromycin (Sugden et al., (1985) *Mol. Cell. Biol.*, 5: 410-413). The three examples given above employ bacterial genes under eukaryotic control to convey resistance to the appropriate drug G418 or neomycin (geneticin), xgpt (mycophenolic acid), or hygromycin, respectively.

(iv) Promoter Component

The expression vector for producing the recombinant protein of interest contains a suitable promoter that is recognized by the host organism and is operably linked to the nucleic acid encoding the polypeptide of interest. Promoters suitable for use with prokaryotic hosts include the beta-lactamase and lactose promoter systems (Chang et al., (1978) *Nature,* 275: 615; Goeddel et al., (1979) *Nature,* 281: 544), the arabinose promoter system (Guzman et al., (1992) *J. Bacteriol.,* 174: 7716-7728), alkaline phosphatase, a tryptophan (trp) promoter system (Goeddel, (1980) *Nucleic Acids Res.,* 8: 4057 and EP 36,776) and hybrid promoters such as the tac promoter (deBoer et al., (1983) *Proc. Natl. Acad. Sci. USA,* 80: 21-25). However, other known bacterial promoters are suitable. Their nucleotide sequences have been published, thereby enabling a skilled worker operably to ligate them to DNA encoding the polypeptide of interest (Siebenlist et al, (1980) *Cell,* 20: 269) using linkers or adaptors to supply any required restriction sites. See also, e.g., Sambrook et al., supra; and Ausubel et al., supra.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

(v) Construction and Analysis of Vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., (1977) *Proc. Natl. Acad. Sci. USA,* 74: 5463-5467 or Messing et al., (1981) *Nucleic Acids Res.,* 9: 309, or by the method of Maxam et al., (1980) *Methods in Enzymology,* 65: 499. See also, e.g., Sambrook et al., supra; and Ausubel et al., supra.

The nucleic acid encoding the recombinant protein of interest is inserted into the host cells. Typically, this is accomplished by transforming the host cells with the above-described expression vectors and culturing in conventional nutrient media modified as appropriate for inducing the various promoters.

Culturing the Host Cells

Suitable prokayotic cells for the practice of the invention are well known in the art. Host cells that express the recombinant protein abundantly in the form of inclusion bodies or in the perplasmic or intracellular space are typically used. Suitable prokaryotes include bacteria, e.g., eubacteria, such as Gram-negative or Gram-positive organisms, for example, *E. coli, Bacilli* such as *B. subtilis, Pseudomonas* species such as *P. aeruginosa, Salmonella typhimurium,* or *Serratia marcescens*. One example of an *E. coli* host is *E. coli* 294 (ATCC 31,446). Other strains such as *E. coli* B, *E. coli* X1776 (ATCC 31,537), and *E. coli* W3110 (ATCC 27,325) are also suitable. These examples are illustrative rather than limiting. Strain W3110 is a typical host because it is a common host strain for recombinant DNA product fermentations. In one aspect of the invention, the host cell should secrete minimal amounts of proteolytic enzymes. For example, strain W3110 may be modified to effect a genetic mutation in the genes encoding proteins, with examples of such hosts including *E. coli* W3110 strains 1A2, 27A7, 27B4, and 27C7 described in U.S. Pat. No. 5,410,026 issued Apr. 25, 1995. For example, a strain for the production of VEGF is *E. coli* stain W3110 having the genotype tonAΔ ptr3 phoAΔE15 Δ(argF-lac)169 degP41 ilvg designated 49B3. See also, e.g., table spanning pages 23-24 of WO2004/092393.

Prokaryotic cells used to produce the recombinant protein of interest are grown in media known in the art and suitable for culture of the selected host cells, including the media generally described by Sambrook et al., *Molecular Cloning, A Laboratory Manual,* Cold Spring Harbor Laboratory Press (Cold Spring Harbor, N.Y.) (2001). Media that are suitable for bacteria include, but are not limited to, AP5 medium, nutrient broth, Luria-Bertani (LB) broth, Neidhardt's minimal medium, and C.R.A.P. minimal or complete medium, plus necessary nutrient supplements. In certain embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol, and dithiothreitol.

Examples of suitable media are given in U.S. Pat. Nos. 5,304,472 and 5,342,763. C.R.A.P. phosphate-limiting media consists of 3.57 g $(NH_4)_2(SO_4)$, 0.71 g Na citrate-$2H_2O$, 1.07 g KCl, 5.36 g Yeast Extract (certified), 5.36 g HycaseSF™-Sheffield, adjusted pH with KOH to 7.3, volume adjusted to 872 ml with deionized $H_2O$ and autoclaved; cooled to 55° C. and supplemented with 110 ml 1 M MOPS pH 7.3, 11 ml 50% glucose, 7 ml 1M $MgSO_4$). Carbenicillin may then be added to the induction culture at a concentration of 50 μg/ml.

The prokaryotic host cells are cultured at suitable temperatures. For *E. coli* growth, for example, the temperature ranges from, e.g., about 20° C. to about 39° C., or from about 25° C. to about 37° C., or at about 30° C.

Where the alkaline phosphatase promoter is employed, *E. coli* cells used to produce the polypeptide of interest of this invention are cultured in suitable media in which the alkaline phosphatase promoter can be partially or completely induced as described generally, e.g., in Sambrook et al., *Molecular Cloning, A Laboratory Manual,* Cold Spring Harbor Laboratory Press (Cold Spring Harbor, N.Y.) (2001). The culturing need never take place in the absence of inorganic phosphate or at phosphate starvation levels. At first, the medium contains inorganic phosphate in an amount above the level of induction of protein synthesis and sufficient for the growth of the bacterium. As the cells grow and utilize phosphate, they decrease the level of phosphate in the medium, thereby causing induction of synthesis of the polypeptide.

If the promoter is an inducible promoter, for induction to occur, typically the cells are cultured until a certain optical density is achieved, e.g., a $A_{550}$ of about 200 using a high cell density process, at which point induction is initiated (e.g., by addition of an inducer, by depletion of a medium component, etc.), to induce expression of the gene encoding the polypeptide of interest.

Any necessary supplements may also be included at appropriate concentrations that would be known to those skilled in the art, introduced alone or as a mixture with another supplement or medium such as a complex nitrogen source. The pH of the medium may be any pH from about 5-9, depending mainly on the host organism. For *E. coli*, the pH is, e.g., from about 6.8 to about 7.4, or about 7.0.

Use of Recombinant Proteins

The polypeptide thus recovered may be formulated in a pharmaceutically acceptable carrier and is used for various diagnostic, therapeutic, or other uses known for such molecules. For example, proteins described herein can be used in immunoassays, such as enzyme immunoassays.

Therapeutic uses for the recombinant proteins obtained using the methods described herein are also contemplated. For example, a growth factor or hormone, e.g., VEGF, can be used to enhance growth as desired. For example, VEGF can be used to promote wound healing of, e.g., an acute wound (e.g., burn, surgical wound, normal wound, etc.) or a chronic wound (e.g., diabetic ulcer, pressure ulcer, a decubitus ulcer, a venous ulcer, etc.), to promote hair growth, to promote tissue growth and repair, etc.

Therapeutic formulations of recombinant proteins are prepared for storage by mixing a molecule, e.g., a polypeptide, having the desired degree of purity with optional pharmaceutically acceptable carriers, excipients or stabilizers (Remington's *Pharmaceutical Sciences* 18th edition, Osol, A. Ed. (1995)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In certain embodiments, the formulations to be used for in vivo administration are sterile. This is readily accomplished by filtration through sterile filtration membranes. Recombinant proteins can be stored in lyophilized form or as an aqueous solution or gel form. The pH of the recombinant protein preparations can be, e.g., from about 4 to 8 (in one embodiment, pH 5.0), although higher or lower pH values may also be appropriate in certain instances. It will be understood that use of certain of the excipients, carriers, or stabilizers can result in the formation of salts of the recombinant protein.

The route of polypeptide administration is in accord with known methods, e.g., topical administration, injection or infusion by intravenous, intraperitoneal, intracerebral, intramuscular, intraocular, intraarterial, or intralesional routes, or by sustained-release systems as noted below. The polypeptide can be administered continuously by infusion or by bolus injection.

Typically for wound healing, recombinant protein is formulated for site-specific delivery. When applied topically, the recombinant protein is suitably combined with other ingredients, such as carriers and/or adjuvants. There are no limitations on the nature of such other ingredients, except that they must be pharmaceutically acceptable and efficacious for their intended administration, and cannot significantly degrade the activity of the active ingredients of the composition. Examples of suitable vehicles include ointments, creams, gels, sprays, or suspensions, with or without purified collagen. The compositions also may be impregnated into sterile dressings, transdermal patches, plasters, and bandages, optionally in liquid or semi-liquid form.

For obtaining a gel formulation, the recombinant protein formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. In certain embodiments of the invention, the gelling agent herein is one that is, e.g., inert to biological systems, nontoxic, simple to prepare, and/or not too runny or viscous, and will not destabilize the recombinant protein held within it.

In certain embodiments of the invention, the polysaccharide is an etherified cellulose derivative, in another embodiment one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. In one embodiment, methylcellulose is the polysaccharide.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, e.g., it comprises about 2-5%, or about 3%, or about 4% or about 5%, of the gel, and the recombinant protein is present in an amount of about 300-1000 mg per ml of gel.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's *Pharmaceutical Sciences* 18th edition, Osol, A. Ed. (1995). See also Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

Sustained-release preparations may be prepared. Suitable examples of sustained-release preparations include semipermeable matrices of solid hydrophobic polymers containing a polypeptide of the invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), poly-lactic-coglycolic acid (PLGA) polymer, and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release polypeptide compositions also include liposomally entrapped polypeptides. Liposomes containing the protein are prepared by methods known per se: DE 3,218,121; Epstein et al., (1985) *Proc. Natl. Acad. Sci. USA*, 82: 3688-3692; Hwang et al., (1980) *Proc. Natl. Acad. Sci. USA*, 77: 40304034; EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamellar type in which the lipid content is greater than about 30 mol. % cholesterol, the selected proportion being adjusted for the most effective therapy with polypeptide.

An effective amount of recombinant protein to be employed therapeutically will depend, for example, upon the therapeutic objectives, the route of administration, and the condition of the patient. Accordingly, it will be necessary for the therapist to titer the dosage and modify the route of administration as required to obtain the most beneficial therapeutic effect. A typical daily dosage might range from about 1 μg/kg to up to 10 mg/kg or more, depending on the factors mentioned above. Typically, the clinician will administer polypeptide until a dosage is reached that achieves the desired effect. A patient can also administer the polypeptide under the guidance of the clinician. The progress of this therapy is easily monitored by conventional assays.

The following examples are offered by way of illustration and not by way of limitation.

EXAMPLES

Example 1: Solubilizing and Refolding of Recombinant Human VEGF Expressed in *Escherichia coli*

Methods

Plasmid for VEGF$_{165}$ Expression—

The plasmid pVEGF171 is designed for the expression of human VEGF$_{165}$ (see, e.g., Leung et al., (1989) *Science*, 246:1306-1309) in the *E. coli* periplasm. Transcription of the VEGF coding sequence is placed under tight control of the alkaline phosphatase (AP) promoter (see, e.g., Kikuchi et al., (1981) *Nucleic Acids Research*, 9:5671-8), while sequences required for translation initiation are provided by the trp Shine-Dalgarno region (see, e.g., Yanofsky et al., (1981) *Nucleic Acids Research*, 9:6647-68). The VEGF coding sequence is fused downstream of the bacterial heat-stable enterotoxin II (STII) signal sequence (see, e.g., Lee et al., (1983) *Infect. Immun.* 42:264-8; and, Picken et al., (1983) *Infect. Immun.* 42:269-75) for subsequent secretion into the *E. coli* periplasm. Codon modifications in the STII signal sequence provide for an adjusted translation level, which results in an optimal level of VEGF accumulation in the periplasm (see, e.g., Simmons and Yansura, (1996) *Nature Biotechnoloy*, 14:629-34). The lambda to transcriptional terminator (see, e.g., Scholtissek and Grosse, (1987) *Nucleic Acids Research* 15:3185) is located downstream of the VEGF translational termination codon. The replication origin, and both ampicillin and tetracycline resistance genes, are provided by the plasmid pBR322. See, e.g., Bolivar et al., (1977) *Gene* 2:95-113.

Cell Homogenization and Refractile Body Preparation—

Whole cell broth from *Escherichia coli* cells producing recombinant protein are homogenized with a microfluidizer or Niro Soavi at pressures greater than 8000 psid. The homogenate is diluted 1:1 with 160 mM MgSO$_4$, 0.0375 dextran sulfate and 1% TRITON™ X-100 prior to harvesting the pellet by centrifugation (BTUX centrifuge, Alfa Laval, Sweden).

Solubilization and Refolding—

The pellet (e.g., 1 gram) is suspended in 4 volumes (e.g., 4 ml) of solubilization buffer: 1M Urea/300 mM arginine, 10 mM Tris or CHES, 5 mM EDTA, pH 11, final concentration, (4 L/kg pellet). The suspension is thoroughly mixed for 1-2 hours at room temperature (15-30° C.). Refolding is initiated by addition of 3 volumes (1:4 v/v) of buffer per volume of solubilization buffer, which results in the final concentration of the refolding buffer being 1 M Urea, 15 mM cysteine, 0.5-2 mM DTT, 100 mM arginine, 10 mM Tris or CHES, 5 mM EDTA, pH 9-10. The mixture is stirred with addition of air or oxygen at a constant volumetric mass transfer coefficient $k_{La}$ (e.g., for air sparging in2.5 L vessel $k_{La}$=0.004 to 0.01 min$^{-1}$, sparging rate is 0.3-3 cc/min/L and mixing speed is 200-400 rpm) for 6-24 hours at room temperature. See FIG. 1 for a time course of refolding. Optionally, VEGF can be stabilized in the refold buffer by adding nitrogen (e.g., 0.3-3 cc/min/L for 2.5 L tank) in place of air after 6 hours. See FIG. 7. The folding is monitored by SDS-PAGE, cation exchange HPLC and rpHPLC chromatography, and/or Heparin HPLC.

A significant reduction in the process volume (5-fold) while maintaining the yield of recovered VEGF dimer is observed by refolding in a high pH buffer containing mild levels of denaturants and reductants. It is expected that that this method is applicable in the refolding of other recombinant protein, e.g., other growth factors.

Example II: Single Step Solubilization and Refolding of Recombinant Human VEGF Expressed in *Escherichia coli*

Solubilization and Refolding—

Figure 6:
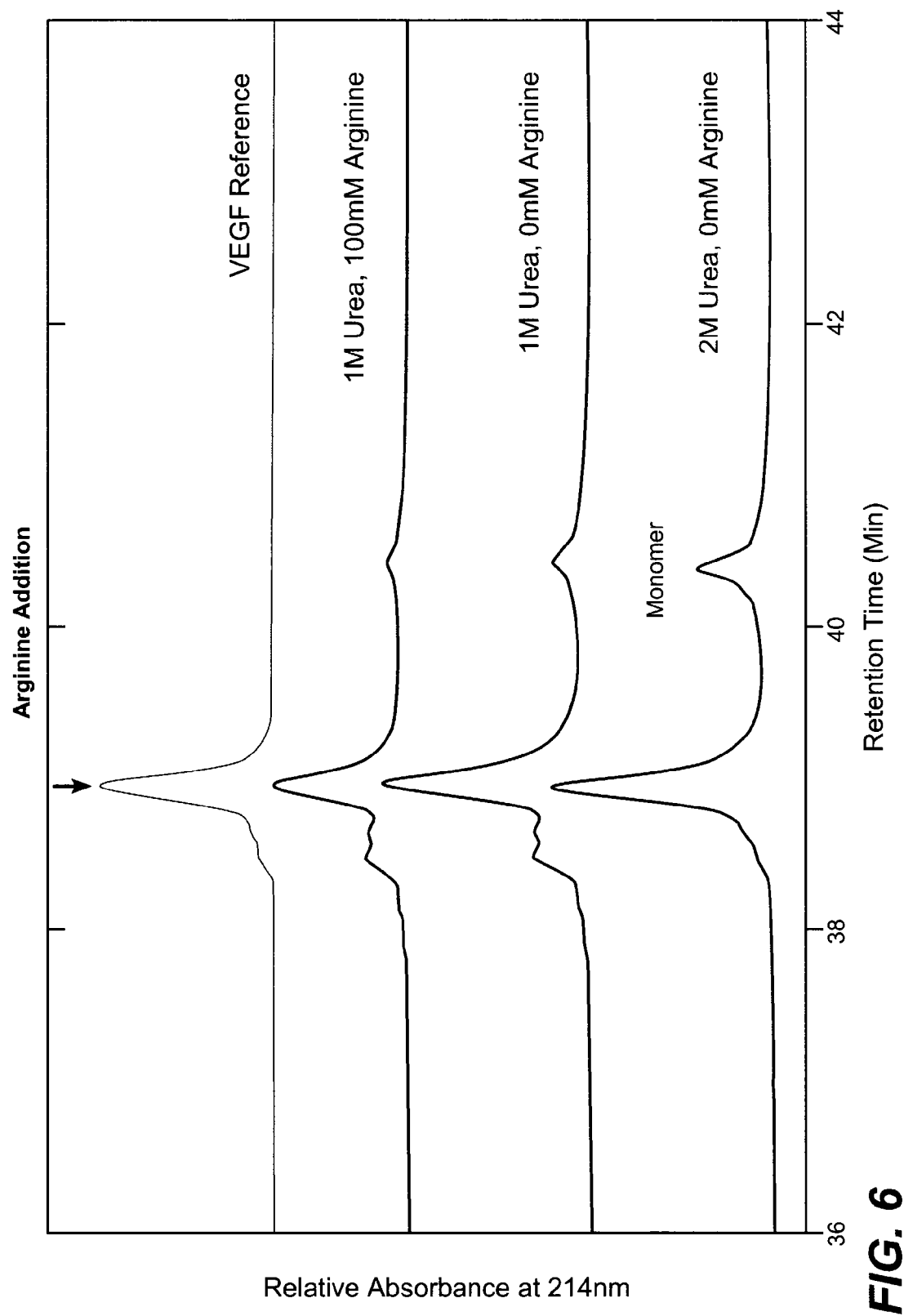
FIG. 6 illustrates the effect of urea and arginine on refolding conditions.

The pellet is suspended in 10-39 liter volumes of refolding buffer (in this case termed "combo buffered solution") for every kg of cell pellet, where the combo buffered solution contains 1 M Urea, 15 mM cysteine, 0.5 or 2 mM DTT, 100 mM arginine, 10 mM Tris or CHES, 5 mM EDTA, pH 9.5-10.5, final concentration. See FIG. 6 for the effect of urea and arginine addition in the refolding buffered solution. FIG. 6 shows the results of a 1-step pellet refold (combo buffered solution) as described in this example at pH 9.5 for 15 hours at room temperature. The denaturant concentrations are varied as follows: (1) 1 M urea and 100 mM arginine; (2) 1 M urea (and 0 mM arginine); (3) 2 M urea (and 0 mM arginine), while all the other buffer components (e.g., Tris or CHES, DTT, etc.) remain in the same concentration. The VEGF titer extracted from these is equivalent as determined by the cation exchange HPLC assay. FIG. 6 shows that the rpHPLC profiles are comparable with or without the presence of arginine.

Figure 7:
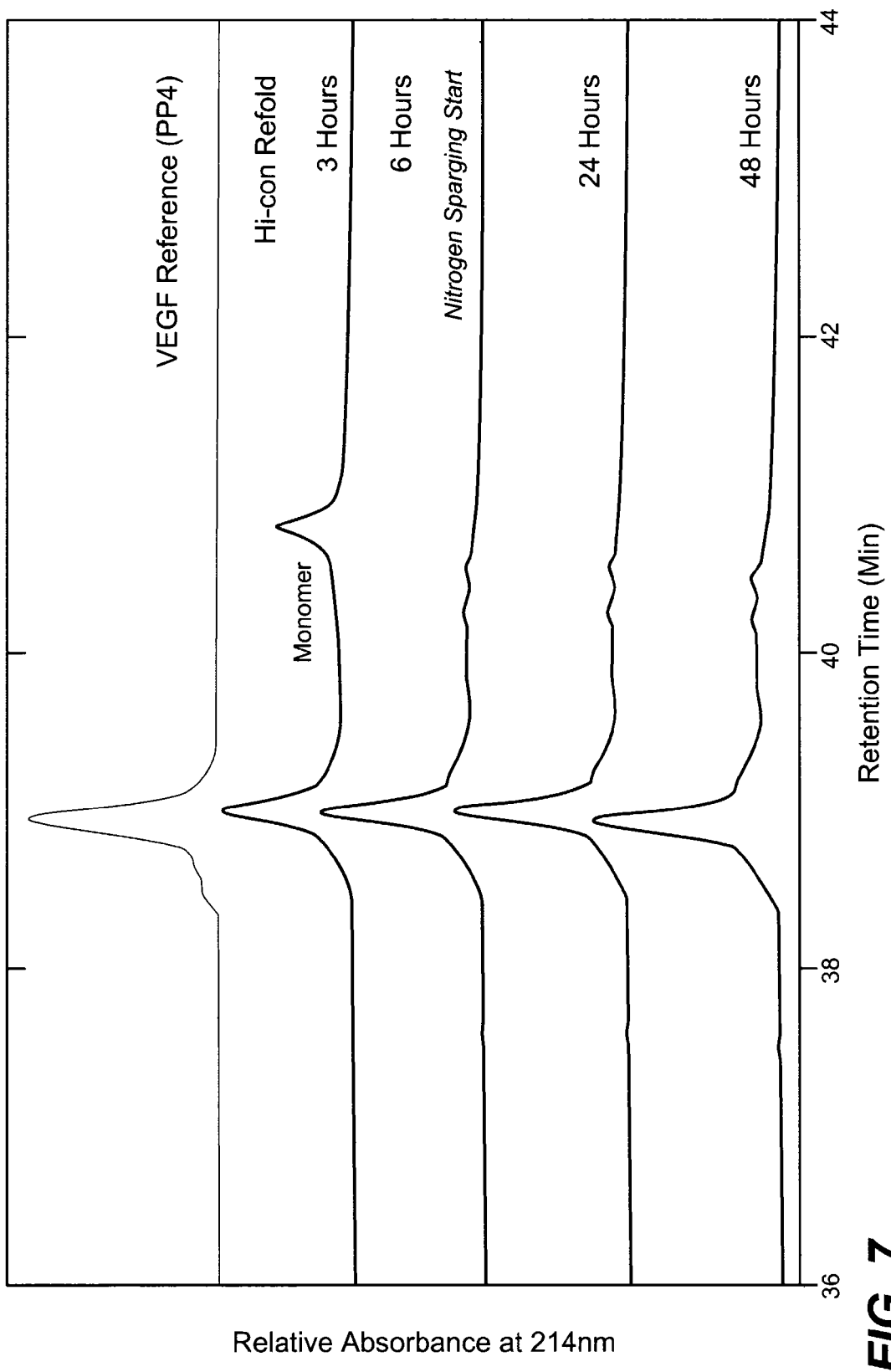
FIG. 7 illustrates the effect of $N_2$ in stabilizing the refold pool up to 48 hours as evaluated by rpHPLC time course, when $N_2$ was added 6 hours after refolding started.
Figure 8:
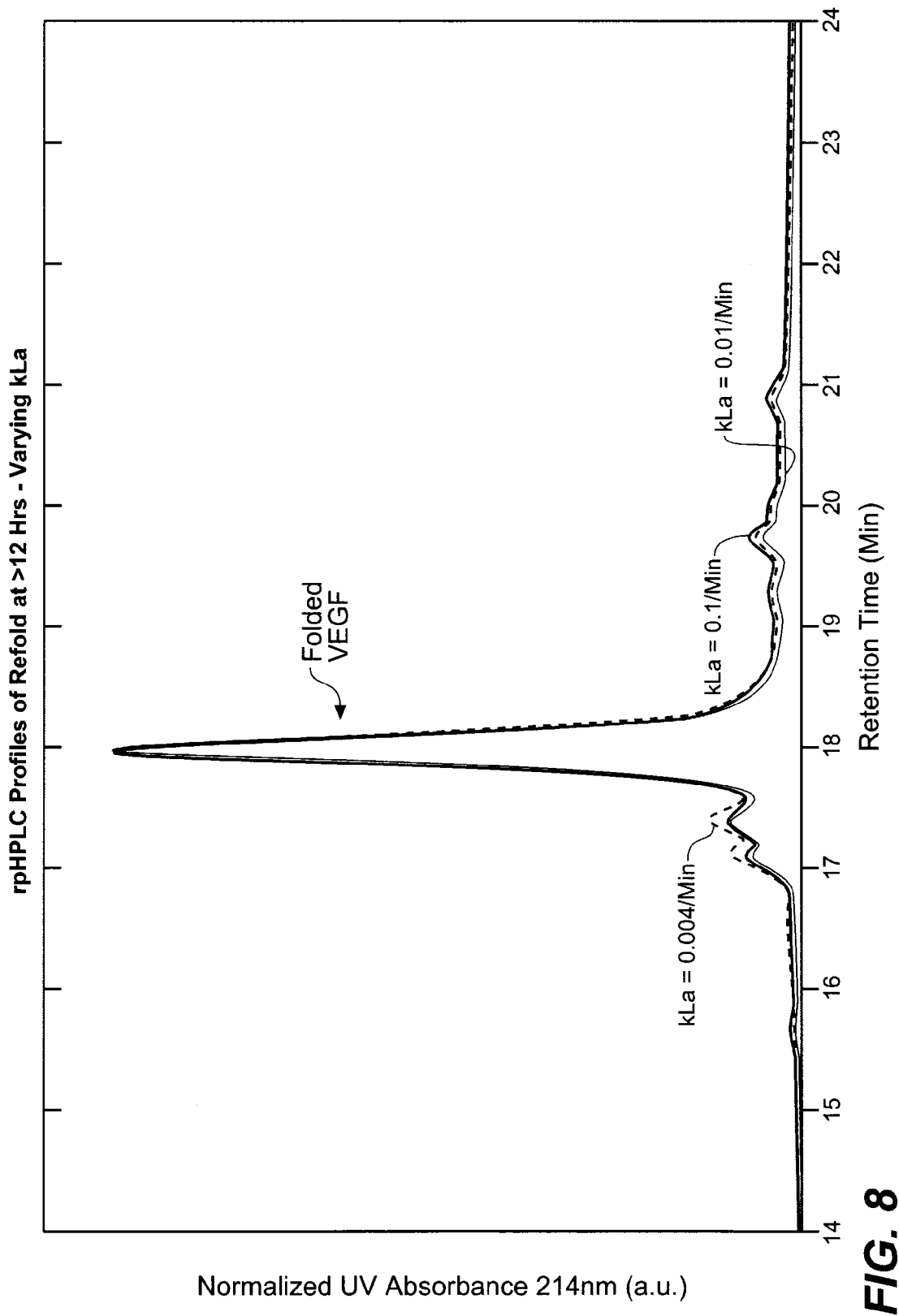
FIG. 8 illustrates the effect of varying air sparging rates on refolding conditions

Solubilization and refolding incubation is conducted at room temperature for 3-24 hours and is sparged with air at a mass transfer coefficient $k_1$=0.004 to 0.1 min$^{-1}$, (e.g., For 2.5 L vessel with marine type impeller, the air sparging rate would be 0.3 to 10 cc/min/L, or 0.3-1 cc/min/L, or 1 cc/min/L, or 25 cc/min/L while mixing is 200-400 rpm). See FIG. 8, for the effects of varying air sparing rates on the refolding conditions. For example, the VEGF containing pellet was added to the combo buffered solution at pH 10 at a ratio of 1:39 (pellet kg to buffer L). Three 2.5 L reaction tanks were prepared and the mixing rate and air sparging rate was varied for each one to achieve a kLa of (a) 0.004, (b) 0.01, (c) 0.1 min−1. The tested mixing rates in each tank were 314 rpm whereas the range for the air sparging was from 1 cc/L/min to 25 cc/L/min. The reactions were monitored over time for yield and product quality. The rpHPLC profiles presented in FIG. 8 show comparable product quality for the resulting folded VEGF after 12 hrs. Optionally, the incubation can be conducted at room temperature for up to about 48 hours. Optionally, VEGF can be stabilized in the refold buffer by adding nitrogen in place of air at the same sparging and mixing rate after 6 hours. See FIG. 7, which shows the results from a 2-step pellet refold (as described in Example I) in the presence of air (e.g., $k_{La}$=0.004 min$^{-1}$ or 0.3 cc/min/L for 2.5 L tank) where at 6 hours the monomer peak is diminished (thus, indicating that the refolding reaction is substantially complete). The air sparging is substituted with N$_2$ (e.g., $k_{La}$=0.004 min$^{-1}$) for up to 48 hours. As seen in FIG. 7, the material remains stable as shown by the rpHPLC traces. The folding is monitored by SDS-PAGE, cation exchange HPLC and rpHPLC chromatography columns, and/or Heparin HPLC.

Example III: Non-Pellet Refolding of Recombinant Protein

*Escherichia coli* whole cell broth producing recombinant protein is homogenized in a model 15 M laboratory homogenizer Gaulin 15M (small scale) or M3 (large scale) (Gaulin Corporation, Everett, Mass.) and diluted 1:4 (v/v) in refolding buffer per volume of homogenate and sparging with air at a mass transfer coefficient $k_{La}$=0.004 to 0.01 min$^{-1}$, (e.g., For 2.5 L vessel with marine type impeller, the air sparging rate would be 0.3 to 3 cc/min/L, or 0.3-1 cc/min/L, or 1 cc/min/L, or 3 cc/min/L while mixing is 200-400 rpm). The refolding buffer contains 1 M Urea, 15 mM cysteine, 2 mM DTT, 100 mM arginine, 10 mM Tris or CHES, 5 mM EDTA, pH 9-10, final concentration. Refold incubation is conducted at room temperature for 3-24 hours. Optionally, VEGF can be stabilized in the refold buffer by adding nitrogen in place of air after 3 hours refold incubation. The folding is monitored by cation exchange HPLC, rpHPLC chromatography, and/or Heparin HPLC.

Example IV: Purification of Recombinant Human VEGF (rhVEGF) after Refolding

Figure 2:
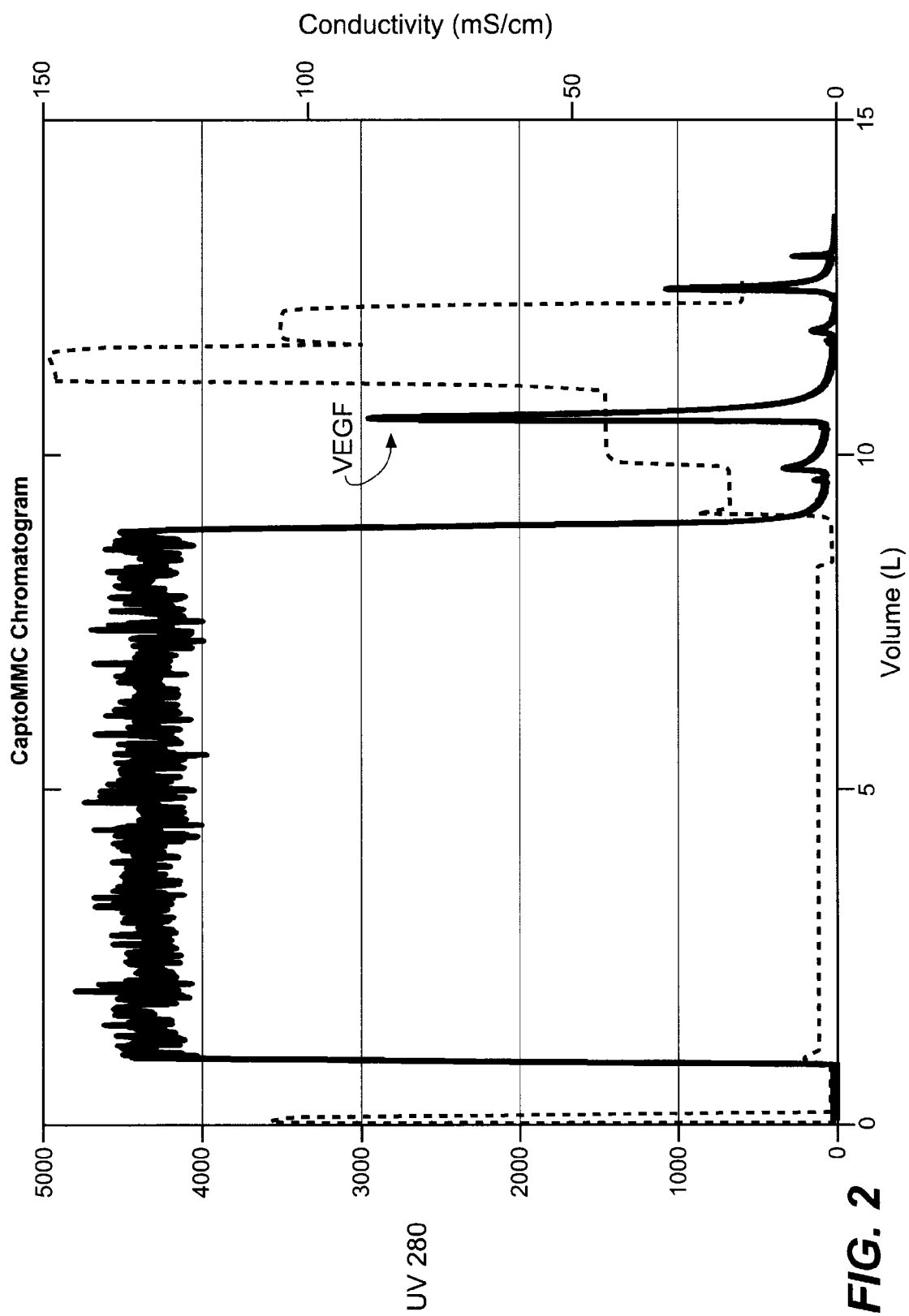
FIG. 2 illustrates a chromatograph from VEGF produced by bacterial strain W3110 loaded on a CAPTOMMC™ column. The column is equilibrated with 25 mM HEPES pH 9.0. The VEGF is eluted from the CAPTOMMC™ column isocratically with 1 M arginine/25 mM HEPES, pH 6-9.

Purification:

The refold pool is clarified by adding TRITON™ X-100 to a final concentration of 1%, adjusting to pH 9 and then centrifugation (10,000×g for 20 minutes at 4° C.). The supernatant is then filtered (Cuno depth filter+0.22 or 0.45μ membrane filter) prior to capture on a mixed mode resin (CAPTOMMC™, GE Healthcare, Piscataway, N.J.) at pH 9 and conductivity <10 mS/cm. Optionally, the refold pool is diluted at least 1:5 in equilibration loading buffer and then filtered (Cuno depth filter+0.22 or 0.45 μmembrane filter) prior to capture on a mixed mode resin (CAPTOMMC™, GE Healthcare, Piscataway, N.J.) at pH 9 and conductivity <10 mS/cm. The packed column is equilibrated with 25 mM HEPES pH 9 prior to loading the sample on the column. The VEGF is eluted from the MMC column isocratically with 1 M arginine/25 mM HEPES, at pH 6-9 (e.g., pH 7.5). See FIG. 2.

Figure 3:
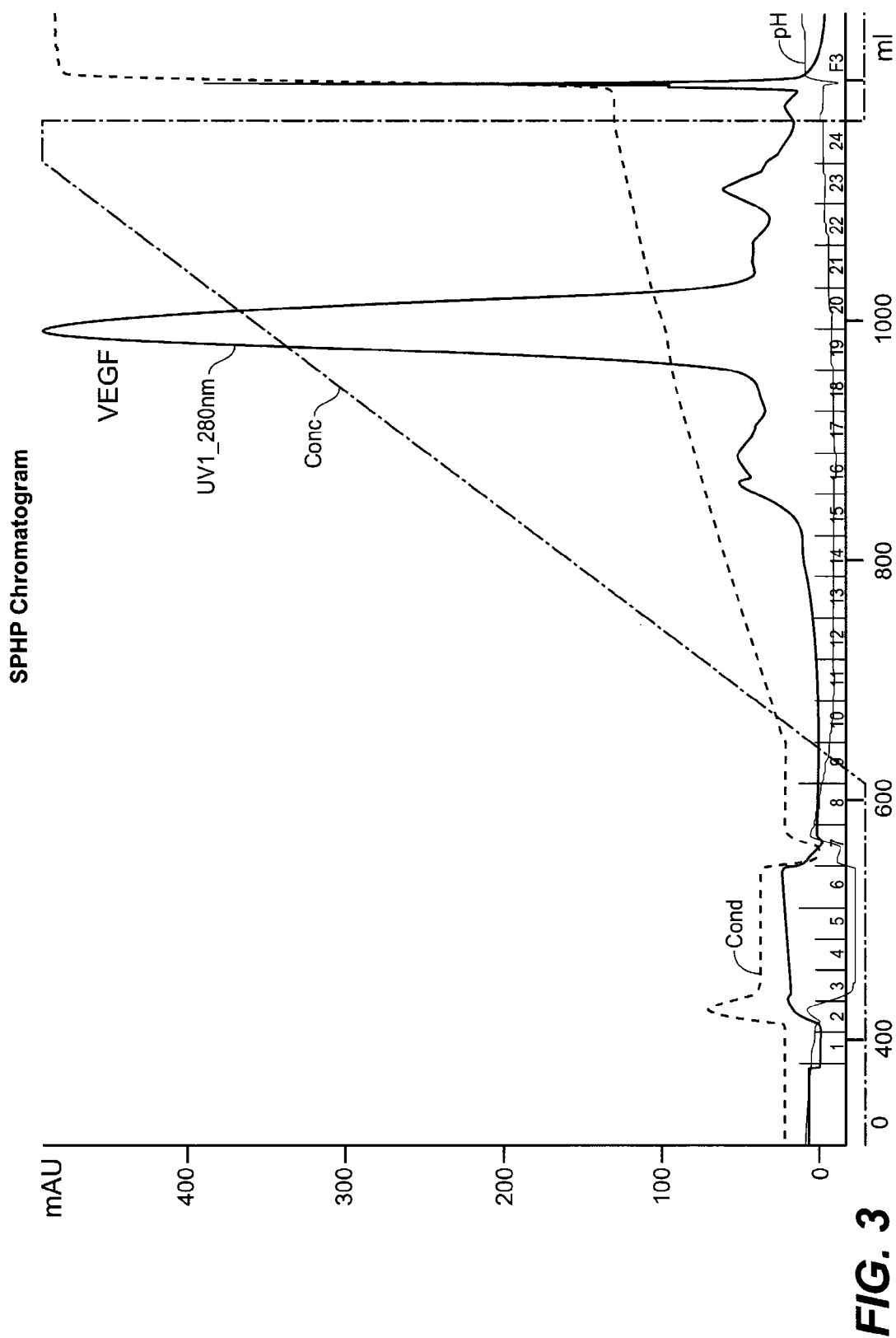
FIG. 3 illustrates a chromatograph from VEGF produced by bacterial strain W3110 loaded on a SPHP column. For example, the SPHP column is equilibrated in 50 mM HEPES, pH 7.5. The column is eluted using a linear gradient from 0.0-1.2 M sodium acetate in, 50 mM HEPES, pH 7.5 over 1 column volume. The eluant is monitored at 280 nm. The protein is recovered from fractions with the highest absorbance at 280 nm (OD max at ~42 mS/cm), which typically contain >90% of the VEGF, are pooled for further processing.

The CAPTOMMC™ pool is adjusted to pH 7.5 with 0.1 N sodium hydroxide and diluted with WFI to 20 mS/cm conductivity prior to loading onto a SP-SEPHAROSE™ HP column (equilibrated with 50 mM HEPES pH 7.5). The VEGF is eluted using a linear salt gradient composed of 50 mM HEPES/0-1.2 M sodium acetate pH 7.5 over 10-20 column volumes (e.g., 15 column volumes) and fractions are collected (1 column volume). The fractions with the highest absorbance @280 nm (OD max at ~42 mS/cm) typically contain >90% of the VEGF and are pooled for further processing. See FIG. 3.

Figure 4:
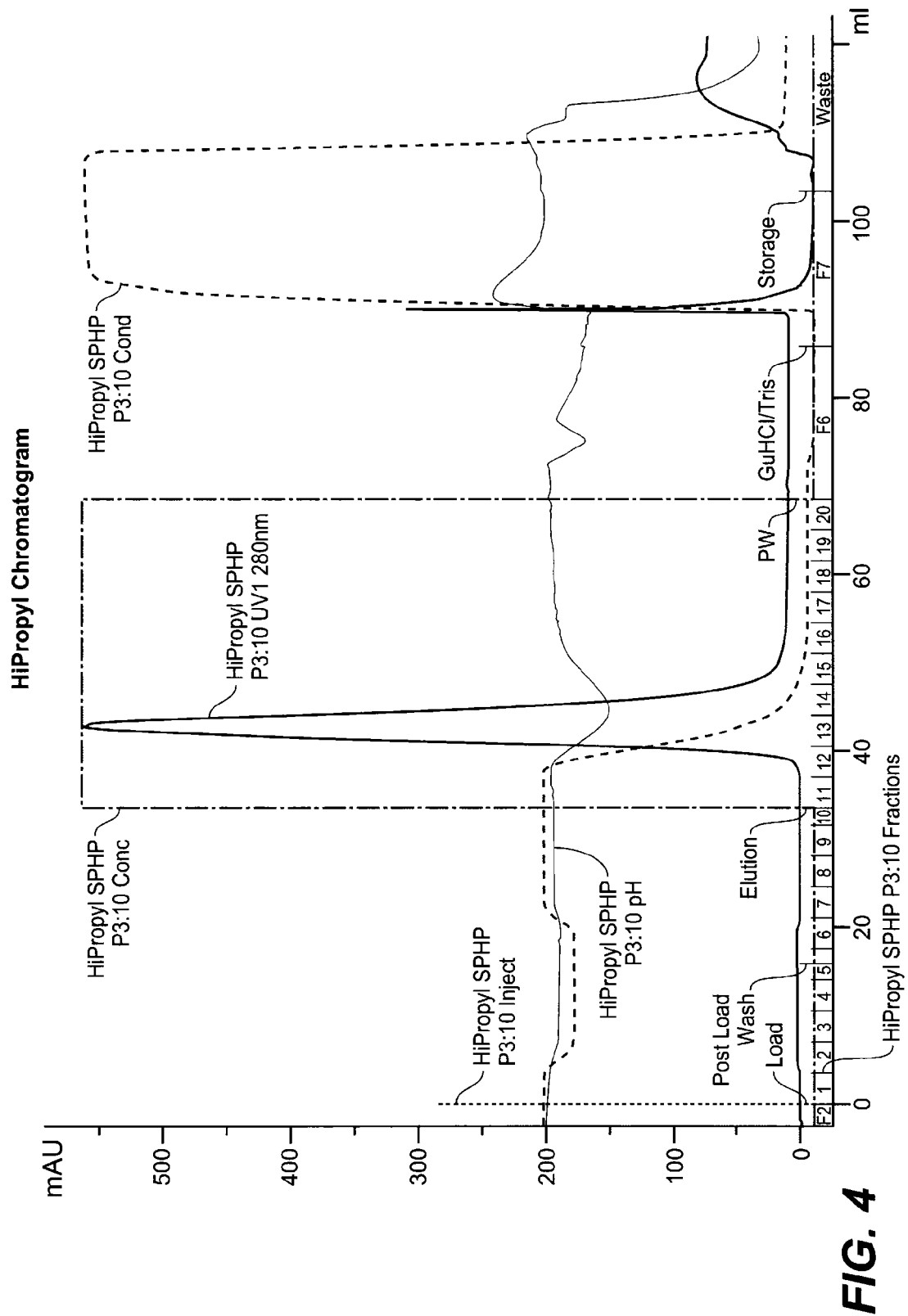
FIG. 4 illustrates a chromatograph from VEGF produced by bacterial strain W3110 loaded on a HI-PROPYL™ column.

The third chromatography step includes a hydrophobic resin (e.g., Hi Propyl, J.T. Baker, Phenyl Sepharose Fast Flow (low sub), GE Healthcare, Piscataway, N.J.). The SP-Sepharose HP elution pool is conditioned to 50 mS/cm conductivity using either sodium acetate or sodium sulfate prior to loading onto the equilibrated column (50 mM HEPES, 1.2 M sodium acetate, pH 7.5). See FIG. 4. The VEGF elutes isocratically into 50 mM HEPES, pH 7.5 and the pool is analyzed for remaining host cell impurities and soluble aggregates. Fractions are collected and those which contained properly-folded VEGF, as determined by assays described herein are pooled. Optionally, an additional chromatography step is performed, e.g., using a second hydrophobic resin (e.g., Phenyl TSK) or ion exchange resin.

Ultrafiltration/Diafiltration—

The pooled VEGF can be ultrafiltered on a 5 kD regenerated cellulose membrane. on a labscale TFF system to a concentration of 6 g/L (UF1). The sample is diafiltrated with 7-14 DV (Diavolume) with 5 mM sodium succinate via TFF system to 10 g/L and then formulated at 5 g/L for storage at −80° C. The formulation buffer used is 5 mM sodium succinate/275 mM trehalose dehydrate/0.01% polysorbate 20/pH 5.0.

Example V: Purification of Recombinant Human VEGF (rhVEGF) after Refolding

Purification:

The refold pool is clarified by adding TRITON™ X-100 to a final concentration of 1%, adjusting to pH 8.5-9.5 (e.g., pH 8.7) and holding at 25-30° C. for 1 to 10 hours prior to centrifugation. After processing on the centrifuge (10,000×g for 20 minutes at 4° C.) to remove the large density particles, the recovered liquid (centrate) is passed thru a series of depth filters and sterile guard (0.22 or 0.45 µmembrane) filters to remove the fine particles. rhVEGF is then captured on a mixed mode resin (CAPTOMMC™, GE Healthcare, Piscataway, N.J.) at pH 8.7 and conductivity <10 mS/cm. The packed column is equilibrated with 25 mM CHES pH 8.7 prior to loading the sample on the column. The VEGF is eluted from the MMC column isocratically with 0.9 M L-arginine HCl/25 mM HEPES, at pH 6-9 (e.g., pH 7.5).

Figure 5:
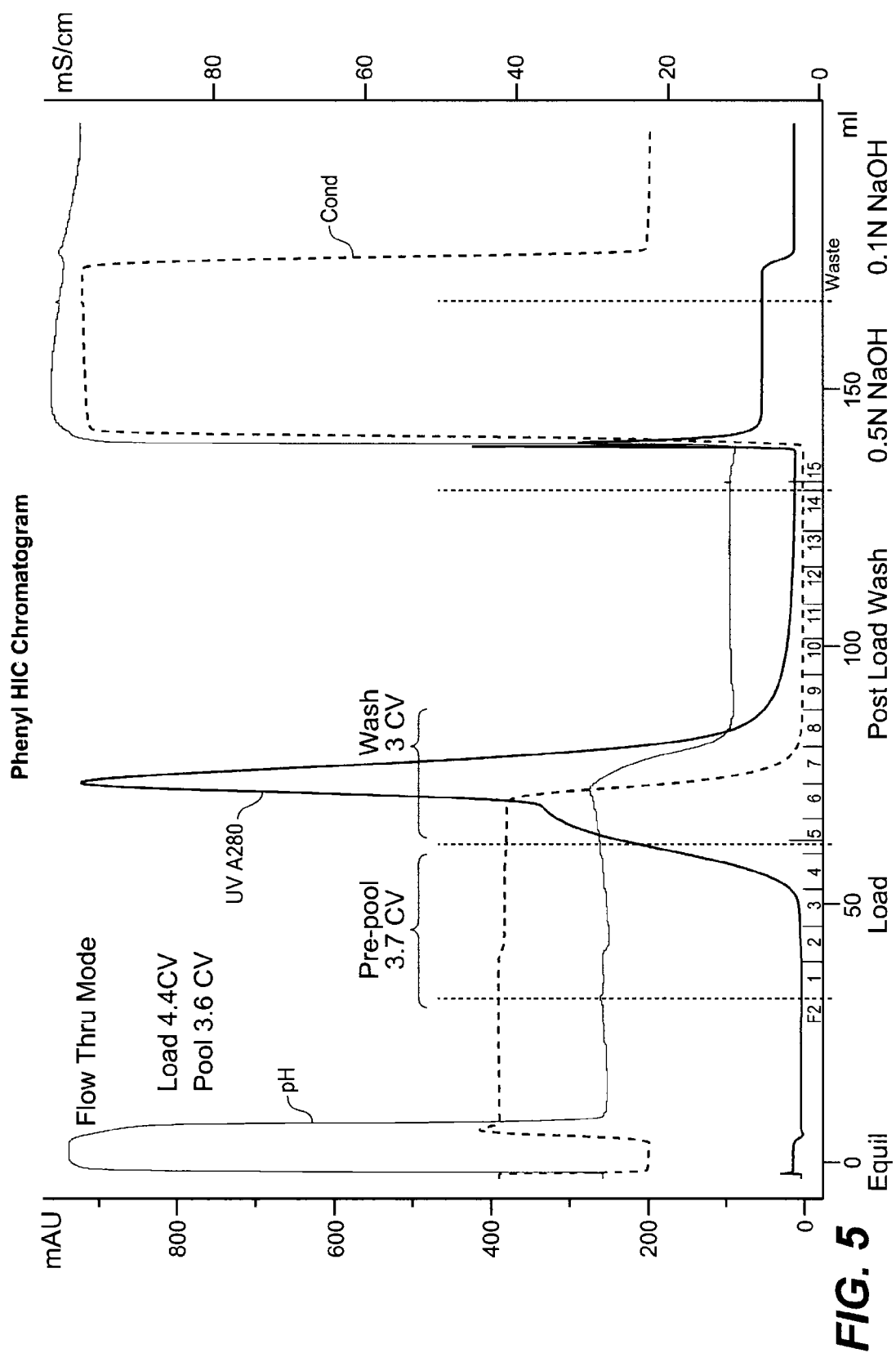
FIG. 5 illustrates a chromatograph from VEGF produced by bacterial strain W3110 loaded on a Phenyl Sepharose column.

The CAPTOMMC™ pool is adjusted to pH 7.5 with 0.1 N sodium hydroxide and diluted with WFI to 20 mS/cm conductivity prior to loading onto a SP-SEPHAROSE™ High Performance column (equilibrated with 25 mM HEPES pH 7.5). The VEGF is eluted using a linear salt gradient composed of 50 mM HEPES/0-1.2 M sodium acetate pH 7.5 over 10-20 column volumes (e.g., 15 column volumes) and fractions are collected (1 column volume). The fractions with the highest absorbance @ 280 nm (OD max at ~42 mS/cm) typically contain >90% of the VEGF and are pooled for further processing. The third chromatography step includes a hydrophobic resin (e.g., HI-PRO-PYL™, J. T. Baker, Phenyl-SEPHAROSE™ Fast Flow (low sub), GE Healthcare, Piscataway, N.J.). The SP-SEPHAROSE™ HP elution pool is loaded directly onto the equilibrated HIC column (25 mM HEPES, 0.75 M sodium acetate, pH 7.5). See FIG. 5. The VEGF elutes isocratically into 50 mM HEPES, pH 7.5 and the pool is analyzed for remaining host cell impurities and soluble aggregates. Fractions are collected and those which contained properly-folded VEGF, as determined by assays described herein are pooled. Optionally, an additional chromatography step is performed to further remove host impurities, e.g., using a second hydrophobic resin (e.g., Phenyl TSK) or ion exchange resin.

Ultrafiltration/Diafiltration—

The pooled VEGF can be ultrafiltered on a 5 kD regenerated cellulose membrane in commercial TFF system (Pellicon 2 casettes, Millipore, Billerica, Mass.) to a concentration of 10 g/L then diafiltered with 7-14 diavolumes (e.g., 10 DV) into the formulation buffer. Final conditioning produces a solution containing 5 g/L VEGF in 5 mM sodium succinate/275 mM trehalose dehydrate/0.01% polysorbate 20/pH 5.0 that can be stored at −80° C.

Example VI: Assays for Determining Folded and/or Purified Recombinant Protein In methods and processes described herein, final purity and/or activity can be assessed by peptide mapping, disulfide mapping, SDS-PAGE (both reduced and non-reduced), circular dichroism, limulus amobocyte lysate (LAL), Cation exchange HPLC, heparin HPLC (e.g., Heparin HPLC can be used to determine VEGF dimer concentration and level of misfolded species), reverse phase (rp) HPLC chromatography (e.g., rpHPLC of reduced samples can be used to determine total VEGF concentration whereas rpHPLC of native samples can assess the quality of refolded VEGF), receptor binding (for example for VEGF e.g., KDR receptor binding-Bioanalytic R&D, and/or Flt1 receptor binding), SEC Analysis, cell assays, HUVEC potency assays, ELISAs with VEGF antibodies, mass spec analysis, etc.

Assay to Determine Total VEGF Expression (1) rpHPLC of Reduced Samples—

The quantity of expressed VEGF is measured using a reverse phase HPLC assay on a C18 column (Jupiter C18 column (4.6×250 mm, 5 micron, by Phenomenex, Torrance, Calif.). The column is equilibrated in 0.22% trifluoroacetic acid and eluted using a linear gradient of 25% to 45% acetonitrile containing 0.2% trifluoroacetic acid in 30 min with a flow rate of 1 mL/min. The eluant is monitored at 280 nm. The sample is treated and fully reduced in guanidine and DTT prior to injection. The reduced VEGF protein elutes around 26 min and the peak area is used to calculate the amount of total VEGF in the sample from a known standard curve.

Assays for Refolded VEGF (1) Cation Exchange HPLC Assay—

Figure 9:
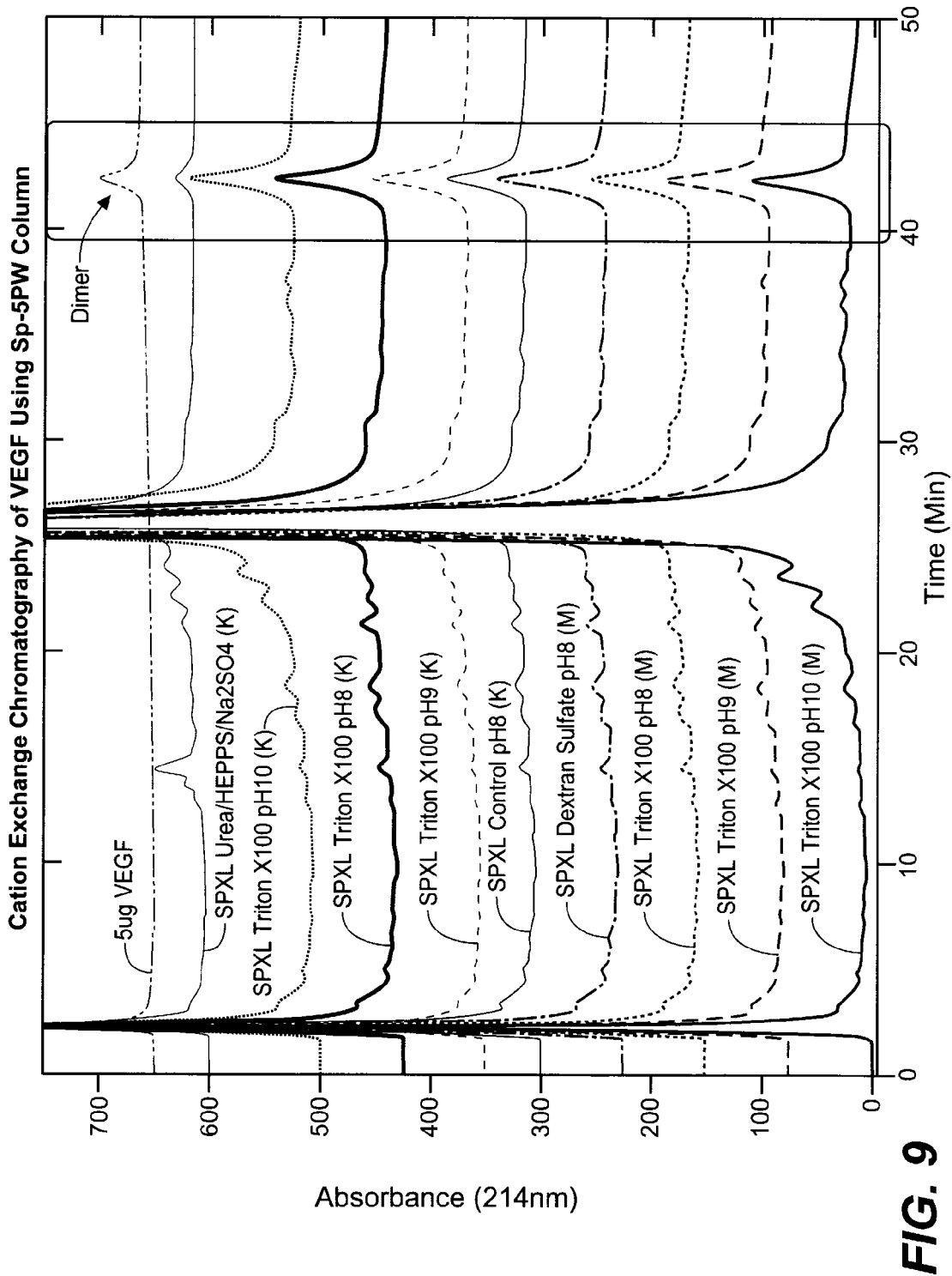
FIG. 9 illustrates a column assay, where cation exchange HPLC is used to assay for refolded VEGF.

The quantity of properly refolded VEGF dimers is determined using an analytical cation exchange column, e.g., SP-5PW column (TSK gel SP-5PW, 7.5×75 mm, 10 micron, by Tosoh Biosciences LLC, Japan). The column is equilibrated in 50 mM sodium phosphate pH 7.5. At a flow rate of 1 mL/min the column is eluted using a linear gradient from 0 to 2 M sodium chloride in equilibration buffer over 60 min. The eluant is monitored at 280 nm or 214 nm. Typically, the majority of protein is eluted in the first 30 min and VEGF is eluted around 40 min. See FIG. 9.

(2) Rp-HPLC Assay—

The quality of properly refolded VEGF is determined using a Zorbax 300SB-C8 column (4.6×150 mm, 3.5 micron, by Agilent Technologies, Santa Clara, Calif.). The column is equilibrated in 0.1% trifluoroacetic acid and eluted using a linear gradient of 0 to 50% acetonitrile containing 0.08% trifluoroacetic acid over 50 min with a flow rate of 1 mL/min. The eluant is monitored at 214 nm. Typically, VEGF elutes around 35 min and the peak profile is evaluated for the percent content of the leading edge hydrophobic species relative to the main peak. Unfolded VEGF monomer elutes 2-3 min later.

(3) Heparin-Binding HPLC Assay—

The quality and quantity of properly refolded VEGF is determined using a column containing immobilized heparin. The column Heparin-5PW (7.5×75 mm, 10 micron, TSK gel by Tosoh Biosciences LLC, Japan) is equilibrated in 10 mM sodium phosphate, pH 7.4 containing 0.15 M sodium chloride. At a flow rate of 1 mL/min the column is eluted using a linear gradient from 0.15 M to 1.6 M sodium chloride in equilibration buffer over 20 min. In some assays, elution is done in 16 min. The eluant is monitored at 280 nm. Typically, the majority of protein is eluted in the void volume and 3 classes of VEGF could be identified. The highest affinity, latest-eluting species is identified as correctly folded VEGF and is sometimes identified as "Peak 3 VEGF."

It is understood that the deposits, examples and embodiments described herein are for illustrative purposes only and that various modifications or changes in light thereof will be suggested to persons skilled in the art and are to be included within the spirit and purview of this application and scope of the appended claims. All publications, citations, patents, and patent applications cited herein are hereby incorporated by reference in their entirety for all purposes.

What is claimed is:

1. A process for recovering a refolded recombinant protein from a prokaryotic cell culture, the method comprising the steps of:
   (a) isolating a recombinant protein from the prokaryotic cell culture;
   (b) solubilizing and refolding said protein in a buffered solution, pH>9 and ≤11, wherein the buffered solution comprises 1 M Urea, 15 mM cysteine, 0.5-2 mM DTT, 100 mM arginine, 10 mM CHES or TRIS, 5 mM EDTA, final concentration, with addition of air or oxygen; and
   (c) recovering said refolded recombinant protein.

2. The process of claim 1, wherein the recovery step comprises clarifying the buffered solution with the recombinant protein and sequentially contacting said refolded recombinant protein to a mixed mode chromatographic support, a cationic chromatographic support, and a first hydrophobic chromatographic support, and selectively eluting the refolded recombinant protein from each support.

3. The process of claim 2, wherein the clarifying step comprises: adding detergent to a final concentration of 1%, adjusting pH to about 8.5-9.5, incubating solution for 1 to 10 hours at 25-30° C., centrifuging the solution, and filtering liquid recovered from the centrifugation step.

4. The process of claim 1, wherein the recombinant protein is incubated in the buffered solution for about 3 to 24 hours.

5. The process of claim 4, wherein the incubation is performed at 2-40° C.

6. The process of claim 2, further comprising contacting said refolded recombinant protein to a second hydrophobic chromatographic support or an ion exchange support and selectively eluting the refolded recombinant protein from the support.

* * * * *

UNITED STATES PATENT AND TRADEMARK OFFICE
CERTIFICATE OF CORRECTION

PATENT NO. : 9,994,612 B2  
APPLICATION NO. : 14/922802  
DATED : June 12, 2018  
INVENTOR(S) : Shelly Pizarro et al.

Page 1 of 1

It is certified that error appears in the above-identified patent and that said Letters Patent is hereby corrected as shown below:

In the Specification

Column 1, Line 9, replace "filed an" with --filed on--.

Column 10, Line 17, replace "NaC1" with --NaCl--.

Column 25, Line 26, replace "$k_1 =0.004$ to $0.1$ min$^{-1}$" with --$k_{La} =0.004$ to $0.1$ min$^{-1}$--.

Column 26, Line 24, replace "0.45 μmembrane" with --0.45 μ membrane--.

Column 27, Line 11, replace "0.45 μmembrane" with --0.45 μ membrane--.

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
            115                 120                 125

Val Gln Asp Pro Gln Thr Cys Lys Cys Ser Cys Lys Asn Thr Asp Ser
        130                 135                 140

Arg Cys Lys Ala Arg Gln Leu Glu Leu Asn Glu Arg Thr Cys Arg Cys
145                 150                 155                 160

Asp Lys Pro Arg Arg
                165
```